(12) United States Patent
Reu et al.

(10) Patent No.: US 12,178,435 B2
(45) Date of Patent: *Dec. 31, 2024

(54) SYSTEMS AND METHODS FOR CATHETER FEEDBACK AND CONTROL FOR AV FISTULA CREATION

(71) Applicant: Avenu Medical, Inc., San Juan Capistrano, CA (US)

(72) Inventors: Gene B. Reu, San Clemente, CA (US); Brad M. Kellerman, Escondido, CA (US); Mark A. Ritchart, Murrietta, CA (US); David K. Wrolstad, Fallbrook, CA (US); David T. Aldridge, Laguna Hills, CA (US); Justin K. Mann, Lake Elsinore, CA (US)

(73) Assignee: Avenu Medical, Inc., San Juan Capistrano, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,479

(22) Filed: Nov. 3, 2023

(65) Prior Publication Data
US 2024/0074757 A1 Mar. 7, 2024

Related U.S. Application Data

(63) Continuation of application No. 17/006,692, filed on Aug. 28, 2020, now Pat. No. 11,844,524, which is a
(Continued)

(51) Int. Cl.
*A61B 17/11* (2006.01)
*A61B 17/00* (2006.01)
(Continued)

(52) U.S. Cl.
CPC .......... *A61B 17/11* (2013.01); *A61B 17/3403* (2013.01); *A61B 18/1492* (2013.01);
(Continued)

(58) Field of Classification Search
CPC .............. A61B 17/00234; A61B 17/11; A61B 17/3403; A61B 2017/1107;
(Continued)

(56) References Cited

U.S. PATENT DOCUMENTS

| | | |
|---|---|---|
| 7,901,400 B2 | 3/2011 | Wham et al. |
| 8,951,276 B2 | 2/2015 | Kellerman et al. |

(Continued)

OTHER PUBLICATIONS

Non-Final Office action for U.S. Appl. No. 15/981,823, filed Apr. 29, 2022, 23 pages.
(Continued)

*Primary Examiner* — Ronald Hupczey, Jr.
*Assistant Examiner* — Bradford C. Blaise
(74) *Attorney, Agent, or Firm* — Stinson LLP

(57) ABSTRACT

A method of operating a catheter assembly including monitoring a gap feedback signal indicative of a distance between a first tissue contact surface and a second tissue contact surface. Producing, via a user interface of the catheter assembly, a graphical depiction of the first tissue contact surface and the second tissue contact surface spaced apart from the first tissue contact surface by the distance. Producing, via the user interface of the catheter assembly, a gap distance warning when the gap feedback signal indicates that the distance is outside of a target gap range.

10 Claims, 21 Drawing Sheets

Related U.S. Application Data continuation of application No. 15/981,823, filed on May 16, 2018, now Pat. No. 11,937,821.

(60) Provisional application No. 62/507,629, filed on May 17, 2017.

(51) Int. Cl.

| | | |
|---|---|---|
| *A61B 17/34* | (2006.01) | |
| *A61B 18/14* | (2006.01) | |
| *A61M 1/36* | (2006.01) | |
| *A61M 25/01* | (2006.01) | |
| *A61M 25/04* | (2006.01) | |
| *A61M 25/06* | (2006.01) | |

(52) U.S. Cl.
CPC ........ *A61M 1/3623* (2022.05); *A61M 1/3655* (2013.01); *A61M 25/0194* (2013.01); *A61M 25/065* (2013.01); *A61B 17/00234* (2013.01); *A61B 2017/1107* (2013.01); *A61B 2017/1139* (2013.01); *A61B 2017/3454* (2013.01); *A61B 2018/1425* (2013.01); *A61M 2025/0197* (2013.01); *A61M 25/04* (2013.01)

(58) Field of Classification Search
CPC .... A61B 2017/1139; A61B 2017/3454; A61B 2018/00404; A61B 2018/00619; A61B 2018/1425; A61B 18/082; A61B 18/1492; A61M 1/3655; A61M 25/0194; A61M 25/04; A61M 25/065; A61M 2025/0197
See application file for complete search history.

(56) References Cited

U.S. PATENT DOCUMENTS

| | | |
|---|---|---|
| 9,138,230 B1 | 9/2015 | Buelna |
| 9,439,710 B2 | 9/2016 | Reu et al. |
| 9,445,868 B2 | 9/2016 | Hull et al. |
| 9,452,015 B2 | 9/2016 | Kellerman et al. |
| 9,474,562 B2 | 10/2016 | Kellerman et al. |
| 9,636,163 B2 | 5/2017 | Lau et al. |
| 11,844,524 B1 * | 12/2023 | Reu .................... A61M 1/3623 |
| 11,937,821 B1 * | 3/2024 | Reu .................... A61B 18/082 |
| 2005/0203504 A1 | 9/2005 | Wham et al. |
| 2005/0209614 A1 | 9/2005 | Fenter et al. |
| 2006/0111704 A1 | 5/2006 | Brenneman et al. |
| 2007/0167941 A1 | 7/2007 | Hamel et al. |
| 2014/0025061 A1 | 1/2014 | Benamou |
| 2014/0114327 A1 | 4/2014 | Boudreaux et al. |
| 2014/0142561 A1 | 5/2014 | Reu et al. |
| 2014/0166727 A1 | 6/2014 | Swayze et al. |
| 2015/0272654 A1 | 10/2015 | Esch et al. |
| 2016/0249914 A1 | 9/2016 | Zhang et al. |
| 2017/0284860 A1 | 10/2017 | Dickerson |
| 2018/0160978 A1 | 6/2018 | Cohen et al. |

OTHER PUBLICATIONS

Final Office action for U.S. Appl. No. 15/981,823, filed Oct. 28, 2022, 26 pages.

Non-Final Office action for U.S. Appl. No. 15/981,823, filed Mar. 15, 2023, 12 pages.

Non-Final Office action for U.S. Appl. No. 15/981,823, filed Aug. 19, 2023, 9 pages.

Non-Final Office action for U.S. Appl. No. 17/006,692, filed Aug. 19, 2022, 17 pages.

Non-Final Office action for U.S. Appl. No. 17/006,692, filed Feb. 16, 2023, 25 pages.

* cited by examiner

| Profile ID: 01 |||||
|---|---|---|---|---|
| Thermal Profile / Fistula Creation Profile |||||
| Thermal Cycle A |||||
| Maximum Number of Pulses: One (1) |||||
| Set Temperature | Hold Time | Max. Duration | Max. Duty Cycle | Audio Tone |
| 350F | 2 sec. | 3 sec. | 45% | Tone 1 |
| 450F | 2 sec. | 3 sec. | 45% | |
| Thermal Cycle B - Gap - Distance Controlled |||||
| Maximum Number of Pulses: Six (6) |||||
| Set Temperature | Hold Time | Max. Duration | Max. Duty Cycle | Audio Tone |
| 600F | 1 sec. | 2 sec. | 45% | Tone 1 |
| 700F | 2 sec. | 3 sec. | 45% | |
| Cool Down Temp. | 8 sec. | 8 sec. | 0% | Tone 2 |
| Thermal Cycle B Plus - Gap - Distance Controlled |||||
| Maximum Number of Pulses: One (1) |||||
| Set Temperature | Hold Time | Max. Duration | Max. Duty Cycle | Audio Tone |
| Cool Down-PWM Off | 1 sec. | 1 sec. | 0% | Tone 2 |
| Thermal Cycle C |||||
| Maximum Number of Pulses: One (1) |||||
| Set Temperature | Hold Time | Max. Duration | Max. Duty Cycle | Audio Tone |
| 600F | 1 sec. | 2 sec. | 45% | Tone 1 |
| 700F | 2 sec. | 3 sec. | 45% | |
| Cool Down Temp. | 8 sec. | 8 sec. | 0% | Tone 2 |
| Removal Pulse |||||
| Thermal Cycle D |||||
| Maximum Number of Pulses: Not Limited (Manually Controlled) |||||
| Set Temperature | Hold Time | Max. Duration | Max. Duty Cycle | Audio Tone |
| 600F | 1 sec. | 2 sec. | 45% | Tone 1 |
| 700F | 2 sec. | 3 sec. | 45% | |
| Cool Down Temp. | 4 sec. | Temp. Regulated | 0% | Tone 2 |

FIG. 10

SYSTEMS AND METHODS FOR CATHETER FEEDBACK AND CONTROL FOR AV FISTULA CREATION

STATEMENT OF RELATED CASES

This application is a continuation under 35 U.S.C. 120 of U.S. application Ser. No. 17/006,692, entitled "Systems and Methods for Catheter Feedback and Control for AV Fistula Creation," filed Aug. 28, 2020 (and which issued as U.S. Pat. No. 11,844,524 on Dec. 19, 2023), which is a continuation under 35 U.S.C. 120 of U.S. Application Ser. No. 15/981,823, entitled "Systems and Methods for Catheter Feedback and Control for AV Fistula Creation," filed on May 16, 2018 (and which issued as U.S. Pat. No. 11,937,821 on Mar. 26, 2024), which in turn claims the benefit under 35 U.S.C. 119 (e) of the filing date of Provisional U.S. Application Ser. No. 62/507,629, entitled "Systems and Methods for Catheter Feedback and Control for AV Fistula Creation," filed on May 17, 2017. Both of these prior applications are expressly incorporated herein by reference, in their entirety.

BACKGROUND OF THE INVENTION

The present invention comprises a device to allow verification, monitoring and control of an arteriovenous (AV) fistula creation catheter which comprises a main housing having a power supply, an embedded electronic controller and a user interface display, and which is configured to allow connection to an intravascular catheter. This application is commonly assigned with and related to U.S. Pat. Nos. 8,951,276, 9,138,230, 9,439,710, 9,445,868, 9,452,015, and 9,474,562, all of which are expressly incorporated by reference herein, in their entirety. The invention described herein is intended for use in conjunction with catheter-based AV Fistula creation systems and methods of the type described and claimed in these identified patents, but is potentially applicable to other types of catheter-based tissue cutting and/or welding systems as well.

SUMMARY OF THE INVENTION

As noted above, the invention described herein is directed to a power controller device and system which allows verification, monitoring, and control of an AV fistula creation catheter which comprises a main housing having a power supply, an embedded electronic controller and a user interface display, and which is configured to allow connection to an intravascular catheter. When activated, the device verifies that a valid catheter is connected, downloads stored manufacturing calibration data from the catheter, and provides a user interface to allow initiation of AV fistula creation. Once creation of the AV fistula is initiated, the device provides closed loop control of the catheter heating element and provides a means of monitoring the catheter temperature and tip position to a prescribed parameter to automate the arteriovenous fistula creation procedure.

In another aspect of the invention, a method of creating an arteriovenous fistula comprising a step of verifying the relative position of the proximal and distal tip of the catheter within the first vessel and second vessel to ensure adequate catheter placement by the practitioner is achieved. Once position verification is complete, the device allows the user to activate the AV fistula creation cycle and provides automated closed loop heating of the catheter heating element and monitoring of the relative position between the catheter distal and proximal tip until the AV fistula creation cycle achieves a prescribed condition and the program is automatically terminated.

More particularly, there is described a method of producing a fistula, which comprises a step of receiving a calibration parameter associated with at least one of a catheter assembly or a heating element coupled to a first tissue contact surface of the catheter assembly, the catheter assembly also including a second tissue contact surface. Further steps include selecting within a control module implemented in at least one of a memory or a processing device and based on the calibration parameter, a control setting associated with the heating element, and sending, from the control module, a first signal to the heating element, the first signal associated with a first temperature set point. Additional steps include changing, within the control module and based on the control setting and a temperature feedback signal, the first signal, receiving a gap feedback signal associated with a distance between the first tissue contact surface and the second tissue contact surface, and sending, from the control module and in response to the gap feedback signal, a second signal to the heating element, the second signal associated with a second temperature set point.

In exemplary methods, the second temperature set point is different from the first temperature set point. When thermal heating cycles are initiated, the first tissue contact surface is in contact with a first tissue wall of a first blood vessel, the second tissue contact surface is in contact with a second tissue wall of a second blood vessel such that the first tissue wall and the second tissue wall are compressed together, and the gap feedback signal is associated with a thickness of the first tissue wall and the second tissue wall compressed between the first tissue contact surface and the second tissue contact surface.

The catheter assembly, in disclosed embodiments, includes a first temperature sensor coupled to the first tissue contact surface and a second temperature sensor coupled to the first tissue contact surface, for the purpose of ensuring maximum reasonable precision as well as redundancy. The utilized temperature feedback signal is based on the higher of a first temperature signal from the first temperature sensor or a second temperature signal from the second temperature sensor. Preventing overheating of the tissue is an important objective.

The control setting is any of a first temperature set point, a duration (i.e., time) set point, a number of iterations of heating, or a duty cycle associated with the first (or heat) signal. The selecting step includes selecting a plurality of control settings associated with the heating element, the plurality of control settings including at least two of the first temperature set point, a duration set point, a number of iterations, or a duty cycle associated with the first signal. The calibration parameter is associated with an identification of a thermal profile that includes the control setting (and any number of other control settings). For example, in some embodiments, the calibration parameter can be an identification of a thermal profile associated with a particular class of patients (e.g., patients of a specific size, patients having a specific arterial profile, or the like).

Prior to the sending of the first signal, a warmup signal may be sent from the control module to the heating element, the warmup signal being associated with a warmup temperature set point.

Further steps of the inventive method may comprise recording, within a lockout module implemented in at least one of the memory or the processing device, a first time stamp associated with one of electronically coupling the catheter assembly to the control module or the sending of the warmup signal, recording, within the lockout module, a second time stamp associated with and before the sending of the first signal to the heating element, and sending to the control module a lockout signal preventing the sending of the first signal to the heating element when a time difference between the second time stamp and the first time stamp exceeds a predetermined lockout time threshold. In this manner, the lockout module can prevent unauthorized re-use of the catheter assembly.

The calibration parameter identified above may be a first calibration parameter, wherein the method further comprises receiving a second calibration parameter, the second calibration parameter associated with a gap feedback sensor within the catheter assembly, the gap feedback sensor configured to produce the gap feedback signal, and validating, within the control module and based on the second calibration parameter, that the gap feedback signal is operational. The control module is included within a housing that is separate from the catheter assembly, and, in an aspect of the invention, the step of receiving the calibration parameter is performed in response to the catheter assembly being electronically coupled to the control module. The catheter assembly may be electronically coupled to the control module via a hard-wired connector coupling, or vial a wireless coupling.

The control module stores a plurality of thermal control settings in memory and the selecting step comprises selecting an applicable thermal control setting from the plurality of stored thermal control settings. The inventive method further comprises a step of automatically limiting the number of signals sent from the control module to the heating element in order to prevent tissue overheating.

A step of generating a control option to permit a user to manually initiate additional thermal pulses to the heating element to assist in removing the catheter from a procedural site is disclosed, which may comprise permitting a user to manually initiate thermal pulses by displaying the control option on a display screen adjacent to a multifunctional button so that activating the button initiates a thermal pulse.

In still another aspect of the invention, a power controller is provided which is configured to be coupled to a catheter assembly, the catheter assembly including a first tissue contact surface, a second tissue contact surface, and a heating element coupled to the first tissue contact surface. The power controller comprises a housing, a power supply within the housing, and an electronic circuit system within the housing. The electronic circuit system includes a startup module implemented in at least one of a memory or a processing device, the startup module configured to receive a calibration parameter associated with at least one of the catheter assembly or the heating element when the catheter assembly is electronically coupled to the power controller. A feedback module is implemented in at least one of the memory or the processing device, the feedback module configured to receive a temperature feedback signal of the first tissue contact surface and a gap feedback signal associated with a sensed distance between the first tissue contact surface and the second tissue contact surface. A control module is also implemented in at least one of the memory or the processing device, the control module configured to A) select a control setting associated with the calibration parameter, from a plurality of stored control settings, based on the calibration parameter, B) send a first signal to the heating element, the first signal associated with a first temperature set point, C) change the first signal based on the control setting and the temperature feedback signal, and D) send, in response to the gap feedback signal, a second signal to the heating element, the second signal associated with a second temperature set point. In most procedures, the second temperature set point is different than the first temperature set point.

The control module is configured to send the first signal to the heating element when the first tissue contact surface is in contact with a first tissue wall of a first blood vessel and the second tissue contact surface is in contact with a second tissue wall of a second blood vessel, such that the first tissue wall and the second tissue wall are compressed together. Thus, the gap feedback signal, representing the distance between the first tissue contact surface and the second contact surface, is associated with a thickness of the first tissue wall and the second tissue wall compressed between the first tissue contact surface and the second tissue contact surface.

The catheter assembly includes a first temperature sensor coupled to the first tissue contact surface and a second temperature sensor also coupled to the first tissue contact surface, and the temperature feedback signal is based on the higher of a first temperature signal from the first temperature sensor or a second temperature signal from the second temperature sensor.

The control setting is any of the first temperature set point, a duration (i.e., time) set point, a number of iterations of heating, or a duty cycle associated with the first (or heat) signal. The calibration parameter is associated with an identification of a thermal profile that includes the control setting (and any number of other control settings). For example, in some embodiments, the calibration parameter can be an identification of a thermal profile associated with a particular class of patients (e.g., patients of a specific size, patients having a specific arterial profile, or the like). The control module is configured to store a plurality of thermal control settings associated with the heating element in memory, the plurality of control settings including at least two of the first temperature set point, a duration set point, a number of iterations, or a duty cycle associated with the first signal and the control module is configured to select one of the stored thermal control settings based on the calibration parameter associated with the heating element. The calibration parameter, in disclosed embodiments, comprises an identification number associated with a combination of the plurality of control settings.

In exemplary embodiments, the power controller comprises a display screen for displaying a graphical user interface to a user during operation of the catheter assembly and a multifunction button, the power controller being configured to enable the user to initiate manual signals to the heating element to assist in removing the catheter from a procedural site.

In some embodiments, a method includes receiving, from an electronic circuit system of a catheter assembly, a calibration parameter associated with a gap feedback sensor. The catheter assembly includes a first tissue contact surface, a second tissue contact surface, and a heating element coupled to the first tissue contact surface. The gap feedback sensor is configured to produce a gap feedback signal associated with a distance between the first tissue contact surface and the second tissue contact surface. The method further includes validating, within a control module implemented in at least one of a memory or a processing device, that the gap feedback sensor is operational based on the calibration parameter. A graphical depiction of the first tissue contact surface and the second tissue contact surface spaced apart from the first tissue contact surface by the distance is produced via a user interface of the catheter controller.

In another aspect of the invention, there is disclosed a method comprising steps of recording, within at least one of a memory or a processing device of a catheter controller, a first time stamp associated with electronically coupling an electronic circuit system of a catheter assembly to the catheter controller, the catheter assembly including a first tissue contact surface, a second tissue contact surface, and a heating element coupled to the first tissue contact surface, and receiving from the electronic circuit system of the catheter assembly a validation signal associated with a catheter assembly. Further steps include receiving a start instruction from a user interface of the catheter controller, the start instruction associated with sending a heat signal to the heating element, and recording, within at least one of the memory or the processing device, a second time stamp associated with the start instruction. A lockout signal is then sent to prevent the sending the heat signal to the heating element when either of A) a time difference between the second time stamp and the first time stamp exceeds a predetermined lockout time threshold or B) the validation signal indicates an error associated with the catheter assembly. In one exemplary embodiment, the predetermined lockout time is about 24 hours or greater.

The validation signal may be associated with at least one of a condition of a switch through which the heat signal is sent, a condition of a temperature sensor of the catheter assembly, or a heating test associated with the catheter assembly. Additional method steps may comprise receiving a calibration parameter associated with a gap feedback sensor, the gap feedback configured to produce a gap feedback signal associated with a distance between the first tissue contact surface and the second tissue contact surface, and producing, via a user interface of the catheter controller, an error message if the calibration parameter indicates an error associated with the gap feedback sensor.

Other steps are disclosed, including producing, via the user interface of the catheter controller, a graphical indication indicating that the electronic circuit system of the catheter system is electronically coupled to the catheter controller. The graphical indication may depict, as an example, a connector of the catheter assembly being connected to a mating port of the catheter controller. Additional steps may include receiving a gap feedback signal associated with a distance between the first tissue contact surface and the second tissue contact surface, and producing, via the user interface of the catheter controller, a gap distance warning when the gap feedback signal indicates that the distance is outside of a target gap range. The gap distance warning may be a graphical depiction of the first tissue contact surface and the second tissue contact surface spaced apart from the first tissue contact surface by the distance. The method may include sending, from the catheter controller, the heat signal to the heating element of the catheter assembly, and producing, via the user interface of the catheter controller, a heat indicator in response to the heat signal.

The catheter assembly may include a temperature sensor coupled to the first tissue contact surface, wherein the method further comprises receiving a temperature feedback signal from the temperature sensor, the heat indicator including a graphical indication associated with the temperature feedback signal. The heat indicator, in some embodiments, includes a graphical depiction and an audible tone, the graphical depiction indicating a hot portion of one of the first tissue contact surface or the second tissue contact surface.

In yet another aspect of the invention, there is disclosed a method which comprises steps of receiving, from an electronic circuit system of a catheter assembly, a calibration parameter associated with a gap feedback sensor, the catheter assembly including a first tissue contact surface, a second tissue contact surface, and a heating element coupled to the first tissue contact surface, the gap feedback sensor configured to produce a gap feedback signal associated with a distance between the first tissue contact surface and the second tissue contact surface, and validating, within a control module implemented in at least one of a memory or a processing device, that the gap feedback sensor is operational based on the calibration parameter. A further step includes producing, via a user interface of the catheter controller, a graphical depiction of the first tissue contact surface and the second tissue contact surface spaced apart from the first tissue contact surface by the distance. The graphical depiction shows at least one of the first tissue contact surface or the second tissue contact surface moving in response to a change in the distance, in some embodiments.

A method step may comprise producing, via the user interface of the catheter controller, a gap distance warning when the gap feedback signal indicates that the distance is outside of a target gap range.

Additional method steps, in some applications, include receiving a start instruction from the user interface, sending, from the control module, a heat signal to the heating element of the catheter assembly, and producing, via the user interface, a heat indicator in response to the heat signal. The catheter assembly includes a temperature sensor coupled to the first tissue contact surface, and the method may further comprise receiving a temperature feedback signal from the temperature sensor, the heat indicator including a graphical indication associated with the temperature feedback signal. The heat indicator may include a graphical depiction and an audible tone, the graphical depiction indicating a hot portion of one of the first tissue contact surface or the second tissue contact surface.

The invention, together with additional features and advantages thereof, may best be understood by referencing the following description in conjunction with the accompanying specifications.

BRIEF DESCRIPTION OF THE DRAWINGS

FIG. 10 is a thermal profile array identifying the parameters for each heating cycle of the thermal profile for an exemplary system power controller constructed in accordance with the principles of the present invention;

DETAILED DESCRIPTION OF THE INVENTION

Figure 1:
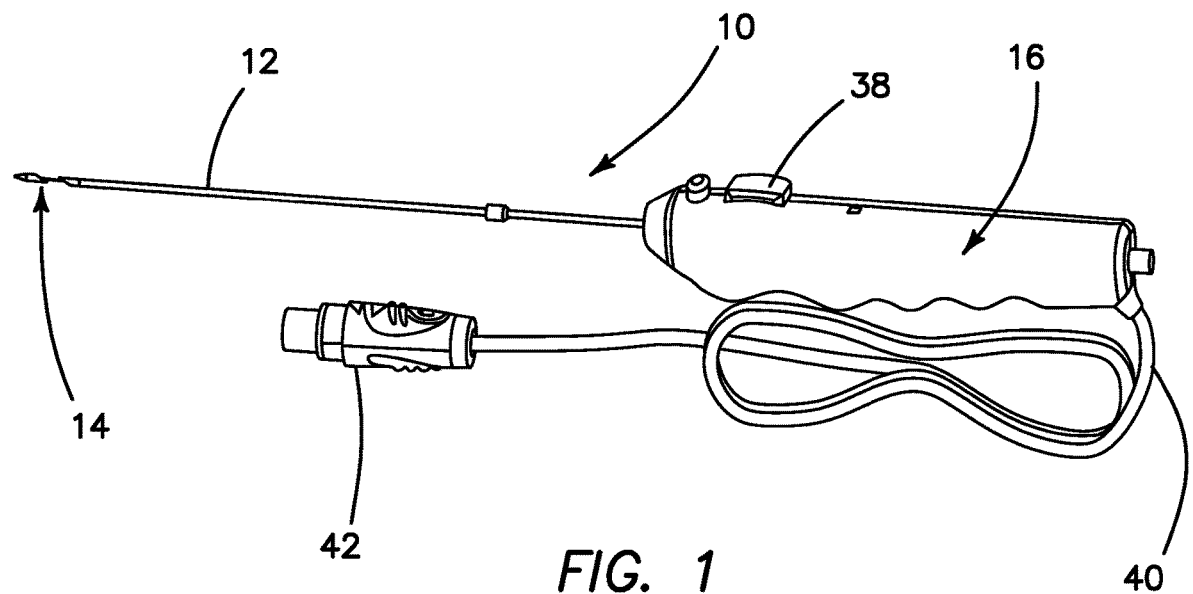
FIG. 1 illustrates an exemplary catheter assembly for use with the power controller system of the present invention.

Now with reference more particularly to the drawings, the invention will be described in greater detail. There is shown in FIG. 1 a vascular access thermal energy catheter assembly 10 comprising a flexible catheter 12 having a heating element on a distal end 14 thereof. The flexible catheter 12 extends distally from a handle 16, which houses various controls for operating the catheter assembly and actuating the distal tip as needed to percutaneously create a vascular anastomosis between adjacent blood vessels 18 and 20 (FIG. 4) using direct current (DC) thermal heating. Such a system 10 is manufactured by Avenu Medical, Inc., of San Juan Capistrano, California, and marketed under the registered trademark ELLIPSYS.

Figure 4:
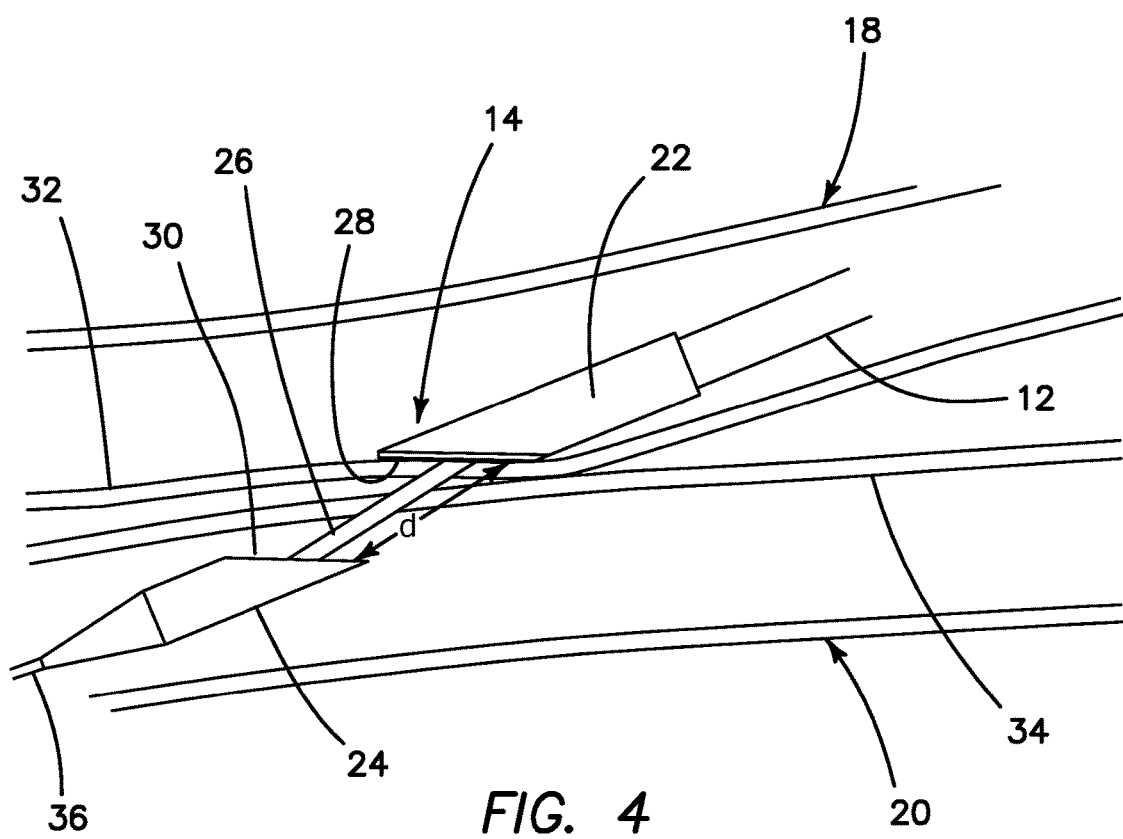
FIG. 4 is a schematic view of the distal portion of the catheter assembly of FIGS. 1, 2, 3A and 3B, at a typical procedural site.
Figure 2:
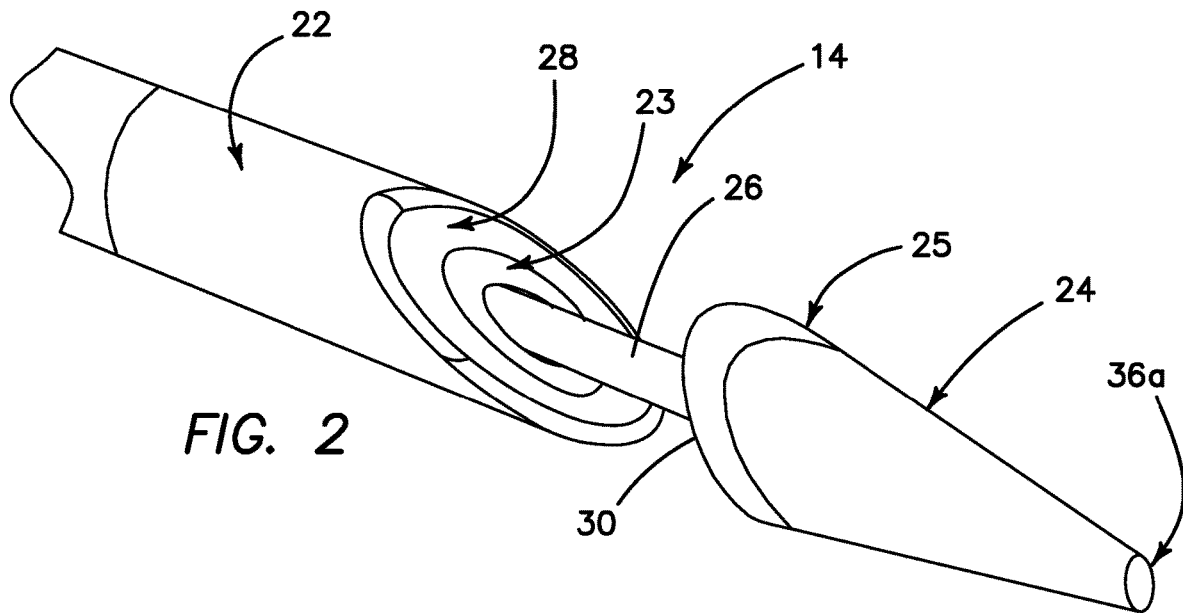
FIG. 2 is an isometric view of the distal end portion of the catheter assembly shown in FIG. 1.
Figure 3A:
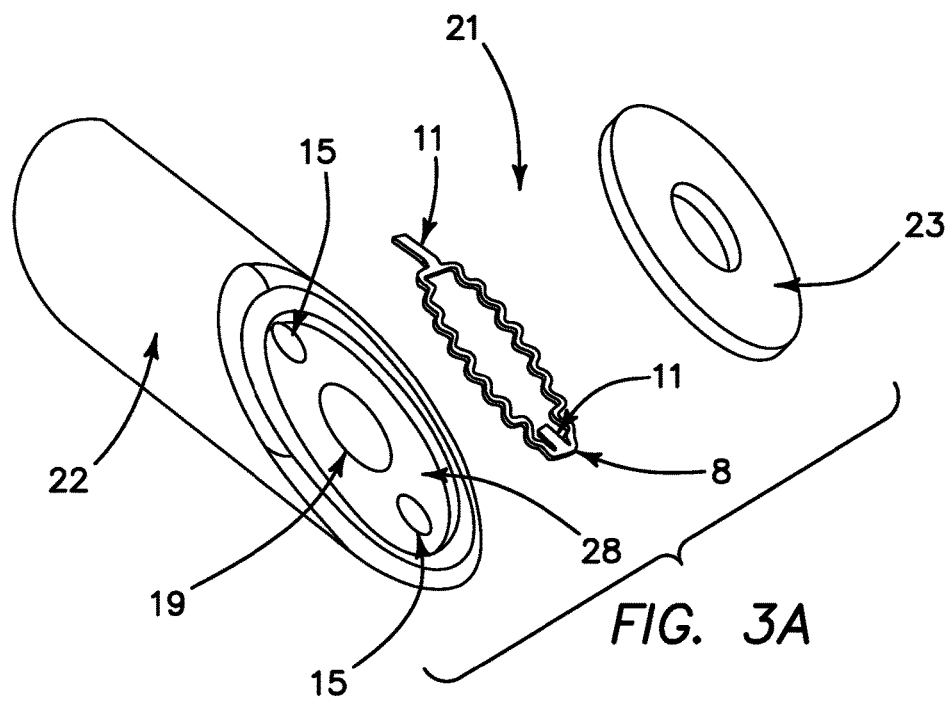
FIG. 3A is an exploded isometric view illustrating the proximal base and particularly showing the assembly of the embedded heater of the catheter assembly shown in FIGS. 1 and 2.
Figure 3B:
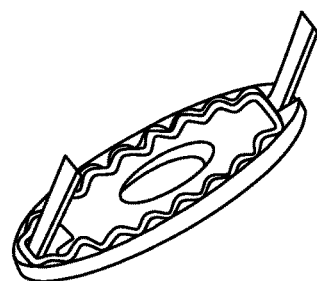
FIG. 3B is an isometric view showing the embedded heater shown in FIG. 3A.

Referring to FIGS. 2, 3A, and 3B, the distal end 14 comprises a proximal member 22 and a distal member 24 joined by a shaft 26. The distal member 24 comprises a heat spreader 25 and terminates in an angled proximal tissue contact surface 30. A guidewire lumen 36*a* extends through the center of the distal member 24, as shown in FIG. 2. The distal member 24 is designed to reside in secondary vessel 20 (FIG. 4) during deployment. The distal member 24 moves with center shaft 26 to desired distance d as shown in FIG. 4. Specifically, the center shaft 26 can slide within a center lumen 19 of the proximal member 22, as shown in FIG. 3A. Movement is generally to bring distal member 24 toward the proximal member 22, thereby capturing vessel wall tissues between the two components 22 and 24 for the purpose of welding the tissues together. As noted above, the proximal end surface 30 of the distal member 24 is angled to match the angle of a distal end tissue contact surface 28 of the proximal member 22. This is designed so that the distal member 24 and the proximal member 22 capture vessel tissue between parallel surfaces, as described below.

The proximal member 22 comprises a distal tissue contact surface 28 and is configured to receive a heating element 8 (FIGS. 4*a* and 4*b*), to form a heating assembly 21 (also referred to as an embedded heater assembly), comprising the heating element 8 and a proximal heat spreader 23. The distal tissue contact surface 28 is comprised of a thermally conductive material which draws heat from heating element 8. Power attachment points 11 ensure that heating element 8 may be energized by a power controller (or catheter controller) by any of the methods described herein. Auxiliary lumens 15 may provide channels for supplying power to the power attachment points 11. The distal tissue contact surface 28 transfers heat into the adjoining vessels to create a weld and/or cut tissue to create an anastomosis or fistula (see FIG. 4). The size and shape of the heating surface 23 mirrors the anastomosis to be created. The thickness of the distal tissue contact surface 28 is approximately the thickness of the vessel in which the weld is being created. However, the thickness may be increased or decreased to control the amount of heat that is conducted into the surrounding tissue. Typical thickness of the heating surface ranges from 0.010 inches to 0.060 inches.

FIGS. 3A and 3B show the construction of embedded heater assembly 21. Heating element 8 has a serpentine configuration to increase length and, therefore, surface area leading to higher energy densities. Heating element 8 is attached inside of a mating cavity from which power attachment leads 11 extend and are inserted into lumens 15 where they are attached to conductors that extend back to handpiece 16.

Although shown as including a heating element 8 in the proximal member 22, in other embodiments, a heating element can be disposed on either one or both of the distal tissue contact surface 28 and proximal tissue contact surface 30.

The proximal member 22 is configured with at least one thermocouple or temperature sensor (not shown) to monitor the temperature near the active heating element 8. As described herein, the temperature of the proximal member 22 is controlled by the power controller using closed loop temperature control to optimize tissue welding and cutting.

As described herein, the catheter assembly 10 provides distal tip feedback, wherein movement of the distal member 24 relative to the proximal member 22 (i.e., to change the distance d as shown in FIG. 4), is converted to a signal by a position sensor within the handpiece 16, or alternatively, outside of handpiece 16. As described, this movement can then be displayed on a user interface and/or utilized for a control algorithm. Specifically, the power controllers described herein can produce a signal that relays the absolute position of the distal member 24 from the position sensor to a display device (not shown) of some type. Such a display is valuable for verifying the tip position throughout the procedure and for determining the thickness of the tissue between the tip and base of the catheter 10 before, during, and after the formation of the fistula. The relative position of the distal member 24 during the formation of the fistula is also valuable and can be related to the rate of tissue dessication, cutting and welding. In some embodiments, this signal may be used as an input to control heat application.

FIG. 4 illustrates the distal end 14 of the catheter assembly 10 in greater detail, as well as its placement at a typical procedural site for the purpose of creating a desired anastomosis. In operation, using a system like the one described herein, a needle system (not shown) is first advanced to the selected procedural site through the first vessel 18, and then is advanced through both the first vessel tissue wall 32 and second vessel tissue wall 34 into the second vessel 20. The needle system is then withdrawn from the procedural site, leaving a guidewire 36 in place.

It should be noted that the catheter assemblies illustrated in FIGS. 1-4 are exemplary only, as the inventive power controller system may be adapted for use with a variety of such assemblies, different ones of which, for example, are shown and described in the aforementioned commonly assigned patents already expressly incorporated by reference herein, and/or sold by the assignee under the trademark ELLIPSYS.

At this point, the catheter assembly 10 is advanced over the guidewire 36 to the procedural site, the practitioner holding the handle 16 to guide the flexible catheter 14 and distal end 10 forwardly. Upon reaching the procedural site, the practitioner uses a control feature 38 on the handle 16 to advance the distal member distally relative to the proximal member, via the shaft 26, through the hole in the tissue walls 32, 34 of the respective vessels 18, 20 until the distal member is fully within the second vessel 20, as shown in FIG. 4. Advancing the distal member 24 causes a gap distance d between the tissue contact surfaces 28 and 30 to increase. Now, the distal member 24 is withdrawn proximally until its proximal tissue contact surface 30 is in contact with the vessel tissue wall 34, while the proximal member 22 is advanced distally until its distal tissue contact surface 28 is in contact with the vessel tissue wall 32. Of course, these relative movements decrease the gap distance d. The blunt shapes of the distal tissue contact surface 28 and proximal tissue contact surface 30 are utilized to push the respective vessel tissue walls 32, 34 together by pushing the proximal member 22 distally while simultaneously retracting the distal member 24 proximally. Once the vessel tissue walls 32, 34 are approximated, the heating element(s) are energized to commence thermal cutting of each adjacent tissue wall 32, 34, and then further energized at a desired setting to weld and thermally seal the tissue boundaries to form the desired anastomosis and complete the procedure.

The foregoing is provided as context to assist understanding of the power controller systems and methods which form the basis of the present inventions. Additional details relating to the catheter-based vascular access system described herein are disclosed in commonly assigned U.S. Pat. Nos. 8,951,276, 9,439,710, 9,452,015, and 9,474,562, all of which are already herein expressly incorporated by reference, in their entirety.

Figure 5:
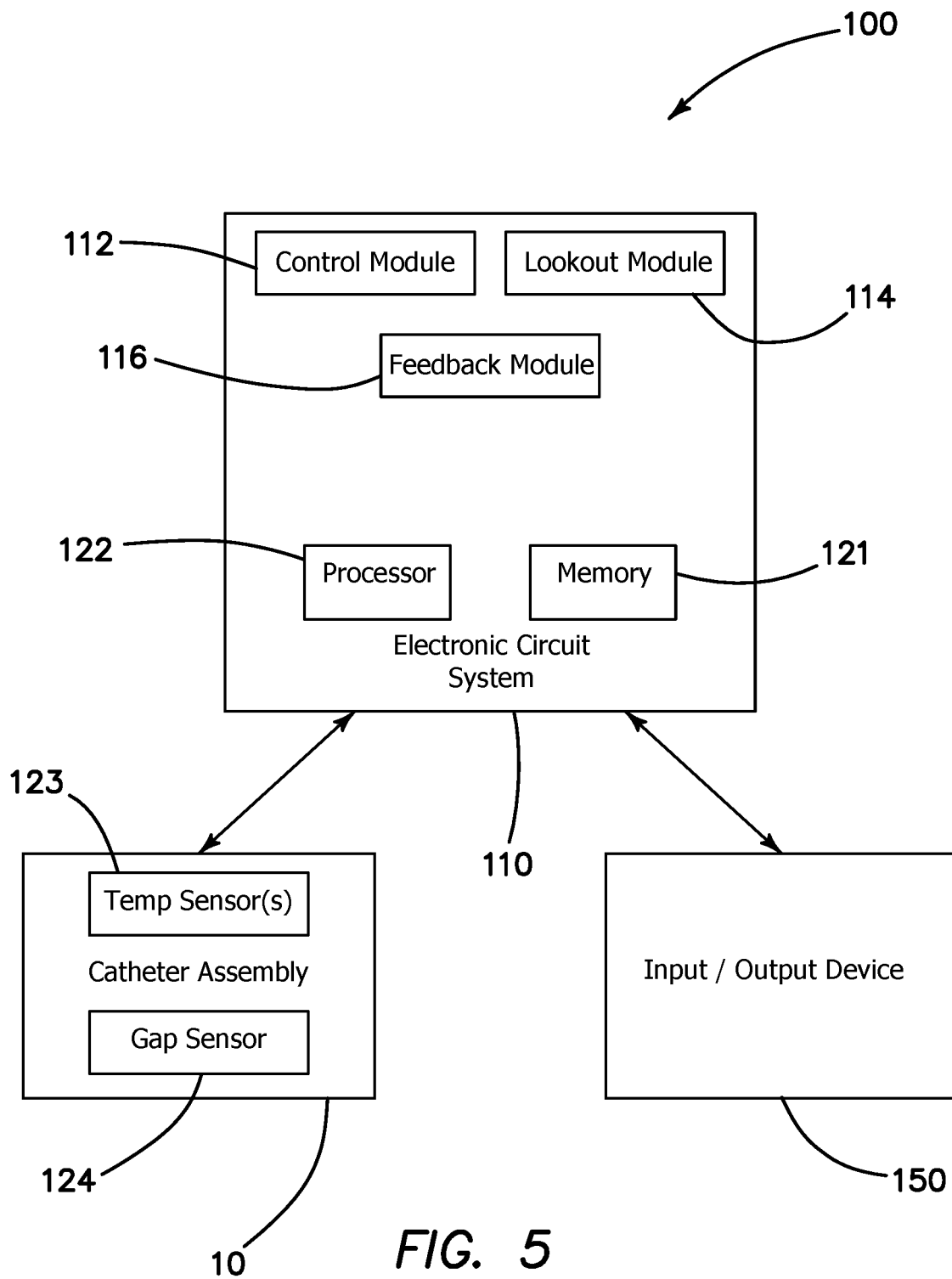
FIG. 5 is a schematic illustration of a power controller of the present invention.

Referring again to FIG. 1, a catheter cable 40 extends from the proximal end of the catheter handle 16 and has a catheter connector 42 at its opposing end. The purpose of the connector 42 is to connect the catheter assembly 10 to a power controller system constructed in accordance with the principles of the present invention and illustrated herein. For example, FIG. 5 is a schematic illustration of a power controller 100 (also referred to as a catheter controller) that can be coupled to (and used with) the catheter assembly 10 or any other suitable catheter assembly of the types shown and described herein. Additionally, the power controller 100 can be coupled to (and used with) any suitable input/output device 150. The input/output device 150 can be, for example, a display screen that is integrated into a common housing along with the other components of the power controller 100. In other embodiments, the input/output device 150 can be a separate a display screen. The power controller 100 can be similar to, and can include any of the hardware shown in, the power controller 44 described below.

Specifically, the power controller 100 includes an electronic circuit system 110 that has a processor 122, a memory 121, and is configured to receive feedback from at least one temperature sensor 123 and a gap feedback sensor 124 of the catheter assembly. Thus, the electronic circuit system 110 also includes a control module 112, a lockout (or startup) module 114, and a feedback module 116. Although shown as including each of these application modules, in other embodiments, a power controller need not include all (or any) of these modules, and can include any other modules described herein. For example, in some embodiments, a power controller includes only a control module 112, and is configured to perform the temperature control methods associated therewith, and need not include the lockout module 114.

The processor 122, and any of the processors described herein can be any suitable processor for performing the methods described herein. In some embodiments, processor 122 can be configured to run and/or execute application modules, processes and/or functions associated with the power controller 100 or the catheter assembly 10. For example, the processor 122 can be configured to run and/or execute the control module 112, the lockout (or startup) module 114, the feedback module 116, and/or any of the other modules described herein, and perform the methods associated therewith. The processor 122 can be, for example, a Field Programmable Gate Array (FPGA), an Application Specific Integrated Circuit (ASIC), a Digital Signal Processor (DSP), and/or the like. The processor 122 can be configured to retrieve data from and/or write data to memory, e.g., the memory 121. The processor 122 can be a set of different processors (e.g., the processors within the System-On Module (SOM) and Microcontroller (MCU), described below) that cooperatively perform the functions and methods described herein.

The memory 121 (and any of the memory devices described herein) can be, for example, random access memory (RAM), memory buffers, hard drives, databases, erasable programmable read only memory (EPROMs), electrically erasable programmable read only memory (EEPROMs), read only memory (ROM), flash memory, hard disks, floppy disks, cloud storage, and/or so forth. In some embodiments, the memory 121 stores instructions to cause the processor 122 to execute modules, processes and/or functions associated with the operation of the catheter assembly 10. For example, the memory 121 can store instructions to cause the processor 122 to execute any of the application modules described herein, and perform the methods associated therewith.

The control module 112 can be a hardware and/or software module (stored in memory 121 and/or executed in the processor 122). As described in more detail herein, the control module 112 is configured to receive a calibration parameter associated with a heating element (or a catheter assembly). In some embodiments, the calibration parameter is received from an electronic circuit system (not shown) of the catheter assembly 10 when the catheter assembly 10 is connected to the power controller 100. For example, in some embodiments, the calibration parameter can be read from a memory of the catheter assembly 10 when the catheter assembly connector 42 is coupled to the power controller. In other embodiments, the calibration parameter can be received from the catheter assembly 10 via wireless transmission. The calibration parameter can be, for example, an identification number associated with a combination of control settings (e.g., temperatures, durations of heating, linear calibration curve of the heater, gain settings, or the like).

The control module 112 is further configured to select, based on the calibration parameter, one or more control settings associated with the heating element 8 and/or the catheter assembly 10. As described above, the control settings can include any suitable parameters used to control the heating during fistula formation. The control settings can include a thermal profile array identifying the parameters for each heating cycle of the thermal profile, as shown in FIG. 10. The control module 112 can then send a first signal to the heating element 8 to initiate heating of the catheter assembly 10 to a first temperature set point. The control module 112 can change, based on the control setting (e.g., a temperature profile) and a temperature feedback signal, the first signal. For example, in some embodiments, the control module 112 can change the first signal to avoid temperature overshoot during creation of a fistula.

In some embodiments, the control module 112 can also modify the heating based on the distance d (also referred to as the "gap") between the proximal member 22 and the distal member 24 (see FIG. 4). For example, the control module 112 is configured to send a second signal to the heating element 8, the second signal being associated with a second temperature set point (e.g., a cool down signal, or the like). The second signal can be sent in response to a gap feedback signal that indicates the distance d.

The lockout (or startup) module 114 can be a hardware and/or software module (stored in memory 121 and/or executed in the processor 122). As described in more detail herein, the lockout module 114 is configured to prevent re-use of the catheter assembly 10 by "timing out" the device after a predetermined time period. For example, the lockout module 114 can record (e.g., within the memory 121) a first time stamp associated with one of electronically coupling the catheter assembly 10 to the power controller 100 or the sending of an initialization (or warmup) signal. The lockout module 114 can further record a second time stamp associated with and before the sending the first signal to the heating element (i.e., at the beginning of a fistula creation procedure). The lockout module 114 can then prevent the power controller 100 and/or the control module 112 from sending any heat signals when a time difference between the second time stamp and the first time stamp exceeds a predetermined lockout time threshold. In this manner, the lockout module 114 can limit the likelihood that the catheter assembly will be reused.

The lockout module 114 can also prevent use of the catheter assembly 10 in other circumstances. For example, in some embodiments, the lockout module 114 can prevent the power controller 100 and/or the control module 112 from sending any heat signals when a validation signal received from the catheter assembly 10 indicates an error condition. Such validation signals can include, for example, a signal indicating an error with a sensor (e.g., a temperature sensor or a gap feedback sensor), an error condition with a switch (e.g., indicating improper functioning of an interlock switch through which the heat signals are conveyed to the heating element 8), an error condition associated with the operation of input/output elements of the power controller 100, failure of the catheter to successfully complete a warmup (or pre-heat) test, or the like.

The feedback module 116 can be a hardware and/or software module (stored in memory 121 and/or executed in the processor 122). As described in more detail herein, the feedback module 116 is configured to receive feedback from the sensors of the catheter assembly 10. The feedback module 116 can include hardware or software filters, A/D converters or the like. Although shown as being included in the power controller 100, in other embodiments, the feedback module 116 can be included in the electronic circuit system of the catheter assembly 10.

Figure 6:
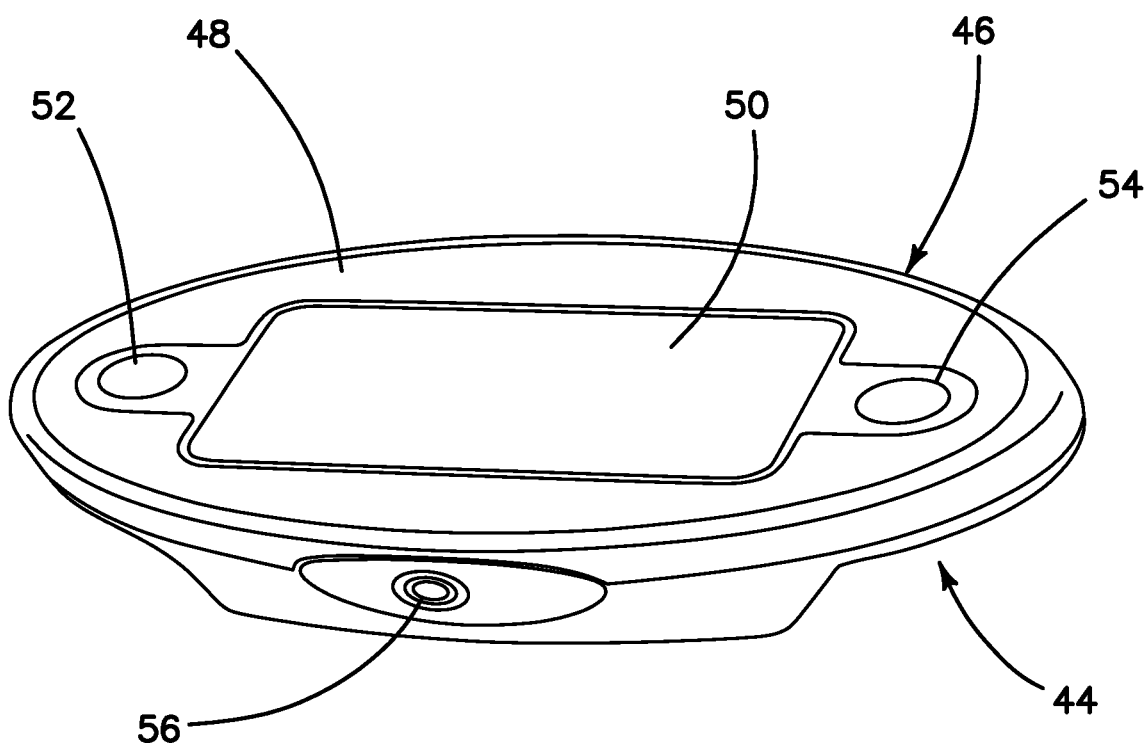
FIG. 6 is an isometric view of an exemplary embodiment of a power controller of the present invention.
Figure 7:
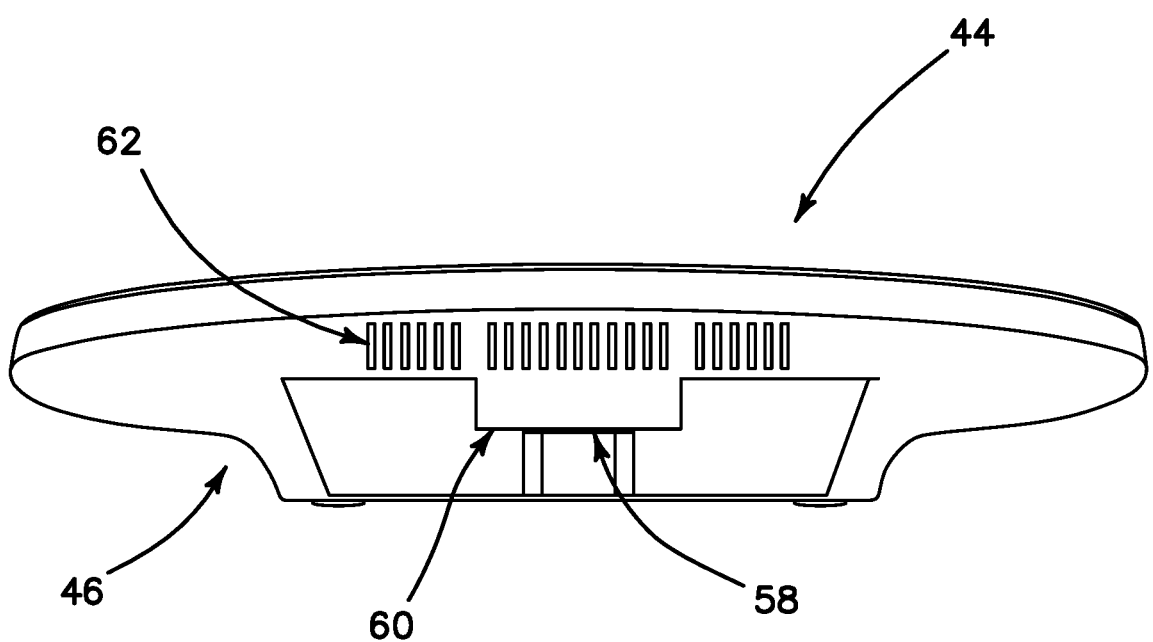
FIG. 7 is an isometric view of the power controller of FIG. 6, illustrating the back panel thereof.

FIGS. 6 and 7 show another embodiment of a power controller. The power controller 44 comprises a reusable, portable, electronic console or housing 46 having a front surface 48 on which is disposed a user interface display screen 50, which may be a Liquid Crystal Display (LCD) screen, as illustrated, or any other suitable user interface display. The console 46 houses internal control electronics, as will be described in detail below, and a D.C. power supply 47. As illustrated in FIG. 6, multifunction buttons 52 and 54 are disposed on either side of the user interface display 50. A catheter connector 56 allows direct connection to the catheter connector 42 on the catheter cable 40. The two multifunction buttons 52, 54 on the face of the controller allow user inputs in response to screen prompts throughout the procedure, as will be discussed below. Inputs are made by depressing the appropriate button 52, 54 adjacent to the icon on the screen 50 for the desired prompt selection. A power input module 58 on the back panel 60 of the console 46 allows the user to connect to mains power using a supplied hospital grade power cord. Vents 62 ensure cooling of the console. The power controller console 46 and its internal control electronics, catheter connection and user interface display is used to convert AC input power to DC power for the catheter heating element and to provide closed loop control of the temperature of the catheter heating element(s) to a system-generated temperature profile.

Figure 8:
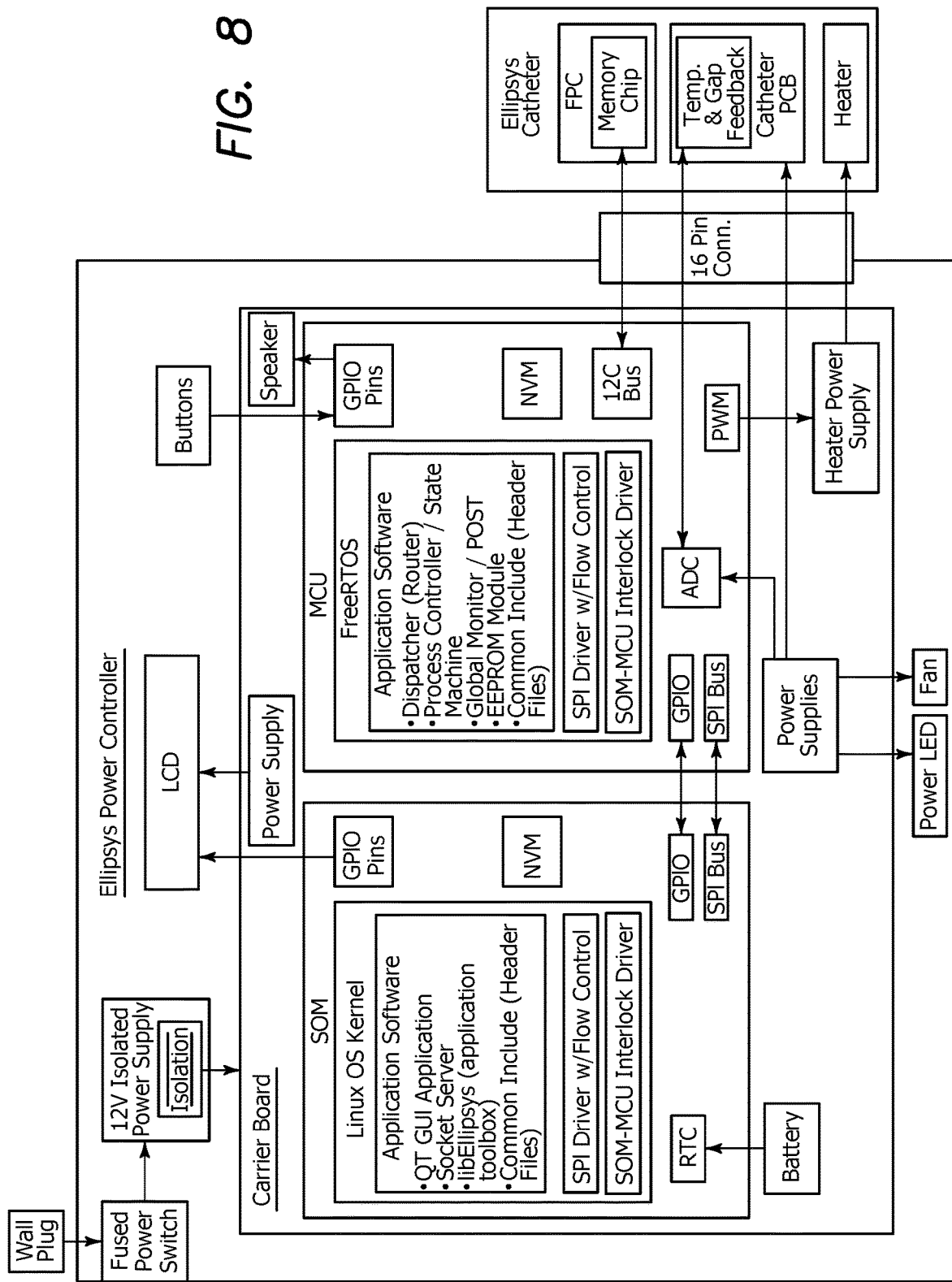
FIG. 8 is a schematic view of an exemplary embodiment of the system architecture for a power controller device and system of the present invention.

FIG. 8 is a schematic representation of the integrated system architecture for the catheter assembly 10 and associated power controller system 44, providing information regarding the interfaces between critical hardware components and the software interfaces on the power controller carrier board.

Figure 9:
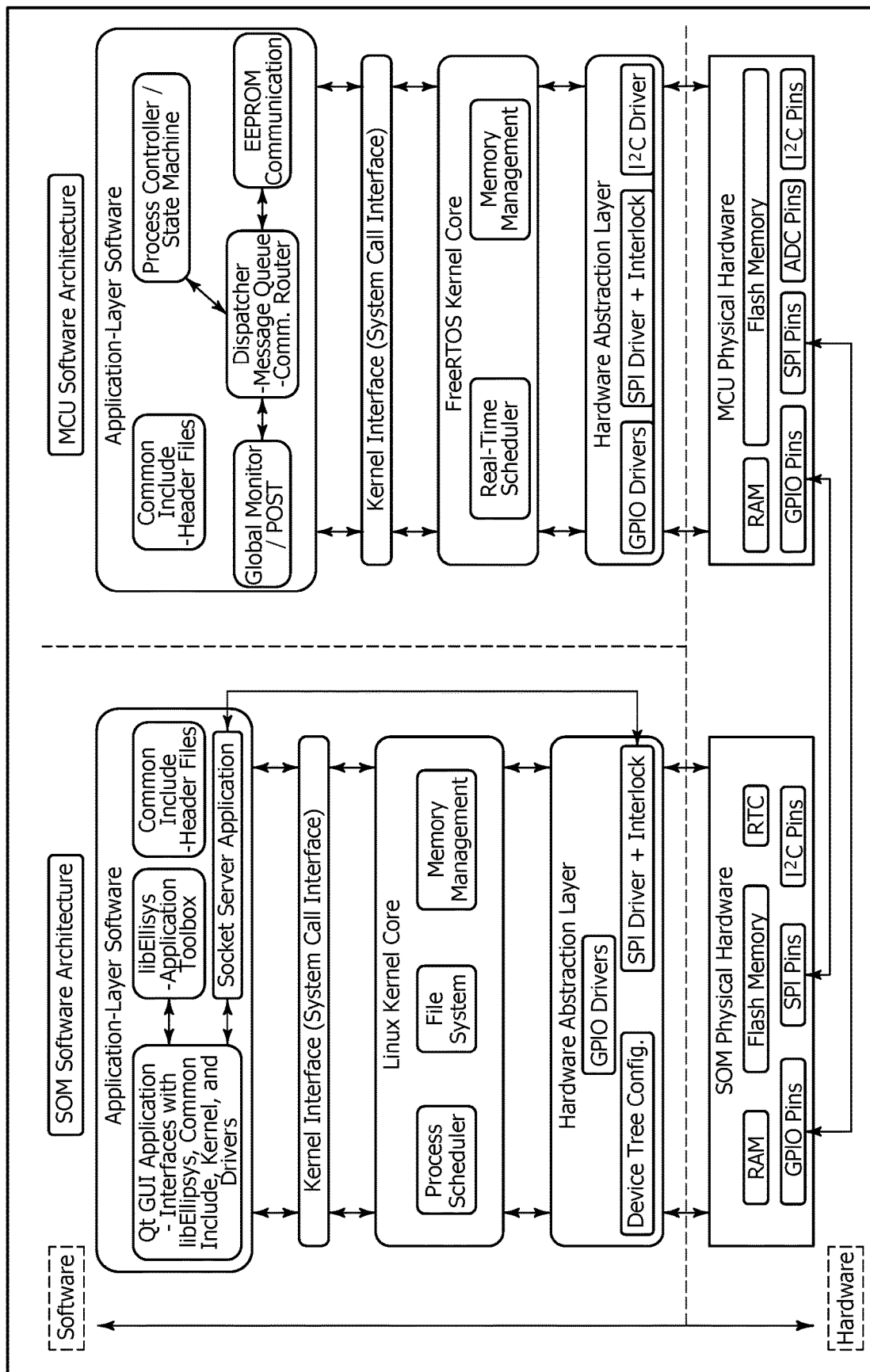
FIG. 9 is a schematic view of an exemplary embodiment of the software architecture supporting the operation and function of the power controller device and system of the present invention.

FIG. 9 is a schematic comprehensive software architecture diagram providing an easily-interpretable reference to the structure of the power controller software elements. Each software unit that has been developed to implement the control logic, feedback monitoring, and procedural guidance for the power controller system are viewable in the diagram. The power controller system 44 can include any of the hardware, firmware, or software as described above with respect to the power controller 100. For example, in some embodiments, the power controller system 44 can include a control module (e.g., similar to the control module 112) that operates in either the System-On Module (SOM) or the Microcontroller (MCU), as described below.

Software Unit Definitions and Functions

Referring to FIGS. 8 and 9, the System Power Controller 44 implements a dual-processor, shared-responsibility processor architecture. Specifically, the power controller 44 includes a System-On Module (SOM) and a Microcontroller (MCU) that each have processors which are capable of functioning independently to verify the performance of the other processor. The SOM processor controls the progress of the procedure utilizing User Interface application software and the Graphical User Interface (GUI), while the MCU records the interrupts from the peripheral devices and controls the real-time procedural steps that implement the Thermal Profile. The dual-processor system is designed as a risk control measure which ensures that no single-point failure in one processor can lead to critical device failures.

The following software architecture description will provide information on the essential functions under the control of the SOM and MCU. Each software element identified in the graphical architecture diagram above will be described briefly below.

SOM Software Units

User Interface and Control Application: The User Interface and Control Application is responsible for generating the Graphical User Interface (GUI) screens, and also for acting as the process control unit on the SOM. The screens, which are displayed to the user via the Liquid Crystal Display (LCD) 50, depict procedural prompts, warnings, and indicators to aid the User throughout the procedure. These screens, in exemplary form, are illustrated in FIGS. 16-33, and will be discussed below.

The GUI application receives communication from the MCU, including event messages, user input (button 52, 54 presses), and global monitoring information. Each screen interprets messages received from the MCU, and then uses control logic to determine the appropriate actions. Actions include transitioning screens, sending commands back to the MCU, and recording information to the Non-Volatile Memory (NVM). The following table lists the inputs and outputs for the User Interface and Control Application.

| User Interface and Control Application | |
|---|---|
| Inputs | Outputs |
| Analog-to-Digital Converter (ADC) values (from MCU) | LCD images |
| Event messages (from MCU) | Start/Stop Event |
| Global monitoring messages (from MCU) | Messages to the MCU | libEllipsys Application: libEllipsys is a shared library which works as an application "toolbox", and contains routines of memory structures and function definitions. It is installed with the software on the SOM, and is called by the User Interface and Control application and other applications to execute.

| libEllipsys | |
|---|---|
| Inputs | Outputs |
| Function calls from User Interface and Control/Socket/SPI | Access to shared sub-routines |

Socket Server Application: The Socket Server is responsible for communicating the messages between the SPI (Serial Peripheral Interface) Driver and any application on the SOM which is requesting message updates. Primarily, the Socket Server will be used to present the real-time update messages from the MCU, including Catheter feedback data, to the User Interface and Control Application which uses that information to control the logical progression of the procedure.

| Socket Server | |
|---|---|
| Inputs | Outputs |
| Data and Event messages outgoing to the MCU (From User Interface and Application) | Messages from the MCU are received, routed, and stored in the RAM on the SOM |
| Messages received from the MCU, routed to the SOM | Messages from User Interface and Control application which are routed to the SPI Driver and then the MCU |

SOM SPI Driver with Flow Control: The SPI driver communication protocol is used to configure the data transfer process between the MCU and the SOM. The SPI Driver communication links user input and peripheral device conditions monitored by the MCU to the Socket Server Application on the SOM.

The flow control is accomplished by two SPI lines which allow each processor to send "Ready-to-Send" and "Clear-to-Send" messages to ensure the other processor is running and ready to receive messages before they are passed. Additionally, the SPI driver interacts with two General Purpose Input/Output (GPIO) boot-pass signal lines which run between the SOM and MCU. The GPIO lines allow the two processor units to communicate and signal that they have successfully completed Boot operations.

| SPI Driver with Flow Control | |
|---|---|
| Inputs | Outputs |
| Data and Event messages from the MCU SPI Driver | Data and Event messages are passed to the Socket Server so that User Interface and Control Application can access the peripheral device and user interface feedback inputs |
| Flow Control Request to Send/Clear to Send (RTS/CTS) messages from the MCU SPI driver | |
| Command messages from the Socket Server (originating from User Interface and Control application) which are directed to the MCU SPI Driver | Command messages are received from the Socket Server (originating from User Interface and Control application) and sent to the SPI Driver on the MCU |
| Voltage on MCU GPIO line which signals that the MCU finished Boot operations | Message queue memory structure which saves messages of each type |
| | Control of a GPIO line which signals to the MCU that the SOM has completed boot operations |

MCU Software Units

Dispatcher (Comm. Router): The Dispatcher on the MCU acts as a central communication Unit which receives messages from the User Interface buttons, the Process Controller, and the Electrically Erasable Programmable Read-Only Memory (EEPROM) Unit, and routes them to their appropriate destination. The Dispatcher also receives all incoming messages from the SPI Driver (originating on the SOM in the User Interface and Control application) and forwards the commands and information to the appropriate Unit on the MCU.

The Dispatcher background processes generate data messages every 5 msec with ADC values and events and sends the message to the SOM through the SPI Driver.

| Dispatcher | |
|---|---|
| Inputs | Outputs |
| Event messages from the Process Controller, User buttons, Global Monitor, and EEPROM Unit | Event messages and procedural data to the EEPROM Unit (to be stored on Catheter) |
| Messages from the SPI Driver (originating in User Interface and Control application) | Commands to the Process Controller/State Machine (from User Interface and Control application/EEPROM) |
| Catheter calibration data from the EEPROM Unit | Button Press event messages to the SPI Driver (routed to SOM and User Interface and Control application) |
| ADC Values from memory (ROM) | System update "interlock" messages every 5 msec (to SOM and User Interface and Control application) |
| | Process Controller update messages to the SPI Driver (routed to SOM and User Interface and Control Application) |

Process Controller/State Machine: The Process Controller/State Machine is responsible for coordinating the real time operations and logic control on the MCU. Real-time events which require access to data from the ADC, including catheter validation testing and control of the catheter Thermal Profile, are mediated by the Process Controller.

The Process Controller shares access to the memory allocation from the ADC channels, which allows the Process Controller to operate the Proportional Integral Derivative (PID) algorithm that regulates the Pulse Width Modulation (PWM) signal output to the heater power supply. The PWM signal in turn controls the power output to the system catheter, regulating the heat of the device. Additionally, the Process Controller is the responsible software unit for implementing the Thermal Profile.

| Process Controller/State Machine | |
|---|---|
| Inputs | Outputs |
| Start/Stop command messages from the Dispatcher (originating from User Interface and Control Application) | Set PID control temp. and control PID Loop |
| | Set audio output tone |
| Recipe parameters (from ROM) | Status/State update messages to Dispatcher (route to User Interface and Control Application on SOM) |
| ADC voltage values (Catheter feedback voltages) | |
| Event messages from Dispatcher | |

Global Monitor/Power-On Self-Test (POST) Unit: The Global Monitor/POST module, or Startup Module, is responsible for monitoring and storing information from the analog voltage channels from the Catheter. The startup module can be similar in function and structure to the lockout module 114 described above. The Gap Distance (identified as "d" in FIG. 4), thermocouple feedback from both channels, and voltage output to the heater are all recorded and stored in the system memory for access by the other software units, including the Process Controller. In typical applications, the catheter is supplied pre-calibrated from the factory and the EEPROM in the connector downloads to the Power Controller once the catheter and Power Controller are connected. The data downloaded to the power controller includes the open and closed positions and a unique thermal profile ID and a checksum. This effectively provides a "hard stop" for the gap distance d, which is used to calibrate and/or validate the electronics, wherein the MCU verifies that the position pre-calibration data on the EEPROM is within the specified range. The unique thermal profile ID (also referred to as a calibration parameter) that is downloaded from the catheter EEPROM at connection tells the MCU which thermal profile (preloaded in the MCU, also referred to as a control setting or set of control settings) to use. This allows multiple thermal profiles to be saved on the power controller MCU for future products, updates, and applications.

On startup, the Global Monitor/POST Unit is responsible for performing a number of system checks to verify the proper function of the device. The POST testing includes calibration of the ADC unit in the processor, power supply voltage monitoring (12V, 8V, 5V, and 3.3V), verification of boot interlock signals, checking NVM for safe mode flags, and functionality testing of the safety interlock switch.

| Global Monitor/POST | |
|---|---|
| Inputs | Outputs |
| ADC calibration result | POST pass/fail message sent to Dispatcher and forwarded to the SPI Driver (routed for SOM and User Interface and Control Application) |
| Boot Interlock pin state | |
| Power supply voltages | |
| RTC verification message from SOM | |
| Safety switch functionality testing result | MCU clock startup |

I²C EEPROM Module: The Inter-Integrated Circuit protocol (I²C) EEPROM module is responsible for coordinating all of the read/write activity between the MCU and the system Catheter EEPROM chip. Event messages and procedural data are passed to the EEPROM module from the Dispatcher on the MCU, and stored to the Catheter EEPROM.

An additional responsibility of the EEPROM module is to read the calibration data from each Catheter prior to use and pass the data to the Dispatcher for processing.

| I²C EEPROM Module | |
|---|---|
| Inputs | Outputs |
| Data and Event messages from the Dispatcher on the MCU Calibration header information from the Catheter EEPROM IC | Data and Event messages are written to the EEPROM chip in the Catheter connector Calibration header messages are passed to the Dispatcher |

MCU SPI Driver with Flow Control: The SPI driver on the MCU is responsible for the communication and data transfer processes between the MCU and the SOM. The SPI Driver receives messages from the Dispatcher on the MCU and sends the messages, which contain user input and peripheral device conditions to the SPI Driver and Socket Server Application on the SOM.

The flow control is accomplished by two SPI lines which allow each processor to send "Ready to Send" and "Clear to Send" messages back and forth to ensure the other processor is running and ready to receive messages before they are passed. Additionally, the SPI driver will interact with the two GPIO boot-pass signal lines which run between the SOM and MCU, and allow the processor units to communicate and signal that they have successfully completed Boot operations.

| SPI Driver with Flow Control | |
|---|---|
| Inputs | Outputs |
| Data and Event messages from the Dispatcher on the MCU Flow Control RTS-CTS messages from the SOM SPI Driver Command messages from the SOM SPI Driver (originating from User Interface and Control Application) Voltage level of SOM GPIO line which signals that the SOM has finished Boot operations | Data and Event messages are passed to the SPI Driver on the SOM so that the Socket Server and User Interface and Control Application can access the peripheral device and user interface feedback Command and Event Messages from the SOM SPI Driver are sent to the Dispatcher Control of a GPIO line which signals to the SOM that the MCU has completed boot operations |

Software Modules and Performance

The software modules or applications described here (in connection with the power controller 44 or the power controller 100) operate to perform any of the functions or methods as described herein. These modules incorporate risk control measures implemented in software, and are defined to a level of detail which satisfies all of the design control specifications for software with a Safety Classification of Class B (from IEC62304). Certain aspects of the modules are described below.

In some embodiments, the power controller 44 (or the power controller 100) can include computer code and can operate using any suitable platform or operating system. For example, in some embodiments, the user interface 50 (or the input/output device 150) can operate using a Linux OS. In some embodiments, the MCU and/or the SOM can operate using a FreeRTOS operating system. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, Fortran, etc.), functional programming languages (Haskell, Erlang, etc.), logical programming languages (e.g., Prolog), object-oriented programming languages (e.g., Java, C++, etc.) or other suitable programming languages and/or development tools. Additional examples of computer code include, but are not limited to, control signals, encrypted code, and compressed code.

Figure 27:
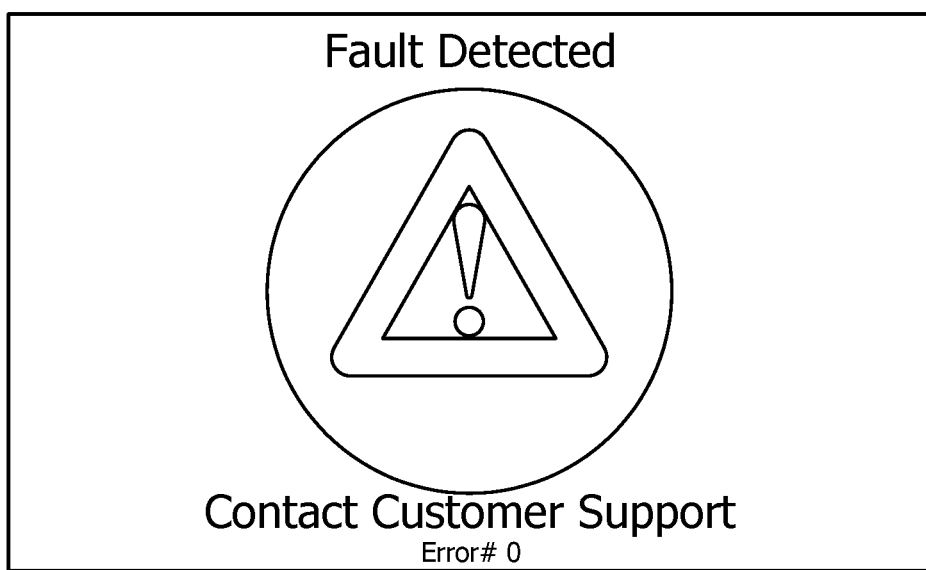
Figure 28:
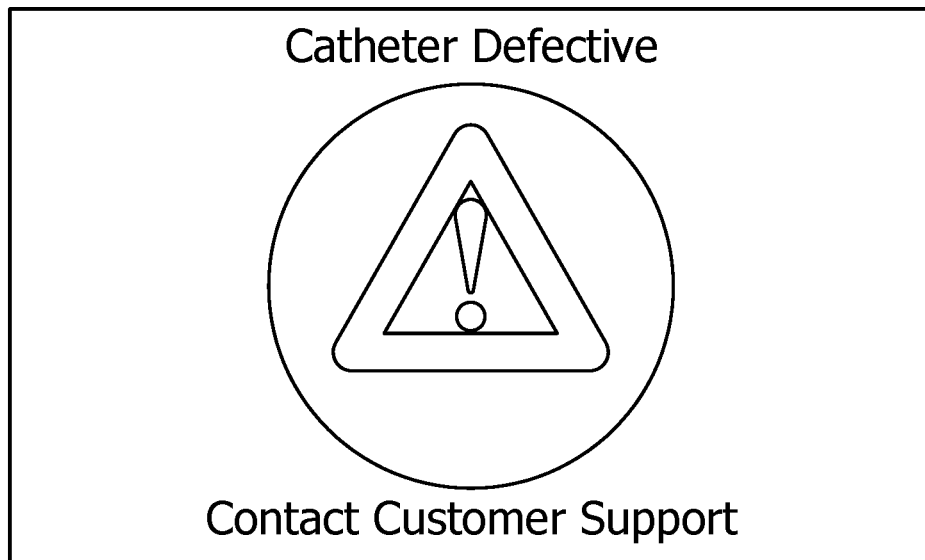

In some embodiments, the lockout (or startup) module can perform a power on startup test (POST). In some embodiments, the lockout (or startup) module functions to verify the real-time clock (RTC) time to determine if it is more recent than the previous boot time. By determining if the current time is not more recent than the previously recorded time, the lockout module can detect if the RTC battery has died. If the RTC battery has died, the lockout module will produce a warning to the user stating that the power controller 44 needs servicing. FIG. 27 shows an image produced on the LCD display 50 indicating a fault condition, such as, for example, a failed RTC battery.

In some embodiments, the power controller 44 includes a safety interlock switch through which the heat signal(s) are sent. The safety interlock switch can be, for example, an FET switch that controls the power output (e.g., pulse width modulated (PWM) signal) to the heater power supply. In some embodiments, the lockout (or startup) module can perform a verification test to determine if the switch is "Off" (open) and "On" (closed) when given the respective control signal from the MCU. The verification test can employ a voltage monitor or any other suitable mechanism for determining the switch state. In response to the switch verification test, the lockout module can send a validation signal that will prompt the power controller 44 display an error and can prevent use of the catheter assembly.

Figure 16:
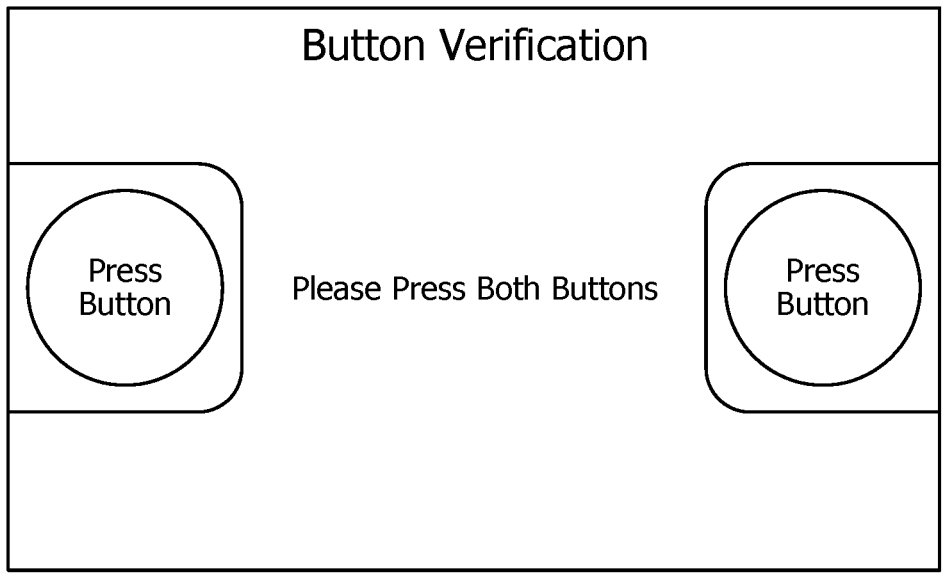
FIGS. 16-33 are various views of the viewing screen of the power controller of the present invention displaying images instructing a user in the operation of the inventive system.

In some embodiments, the lockout (or startup) module can perform a functional test to determine that the input/output device(s) (e.g., the buttons 52, 54 or the input/output device 150) are functioning properly. In some embodiments, lockout (or startup) module can prompt the user to press and hold multiple input devices at the same time (e.g., press and hold both button 52 and 54 simultaneously). In this manner the lockout module can prevent a user from inadvertently advancing to a fistula creation operation. For example, in such embodiments, the lockout module (or control module) will prevent the user from continuing (e.g., either to the catheter connection prompt or a heat delivery prompt) unless both buttons are pressed. FIG. 16 shows an image produced on the LCD display 50 prompting the user to press and hold both buttons.

Figure 17:
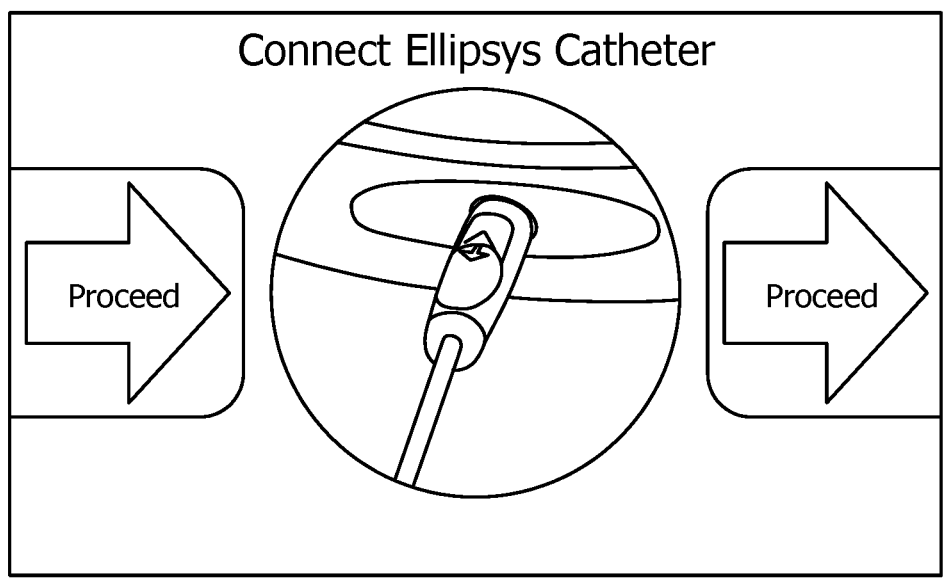
Figure 25:
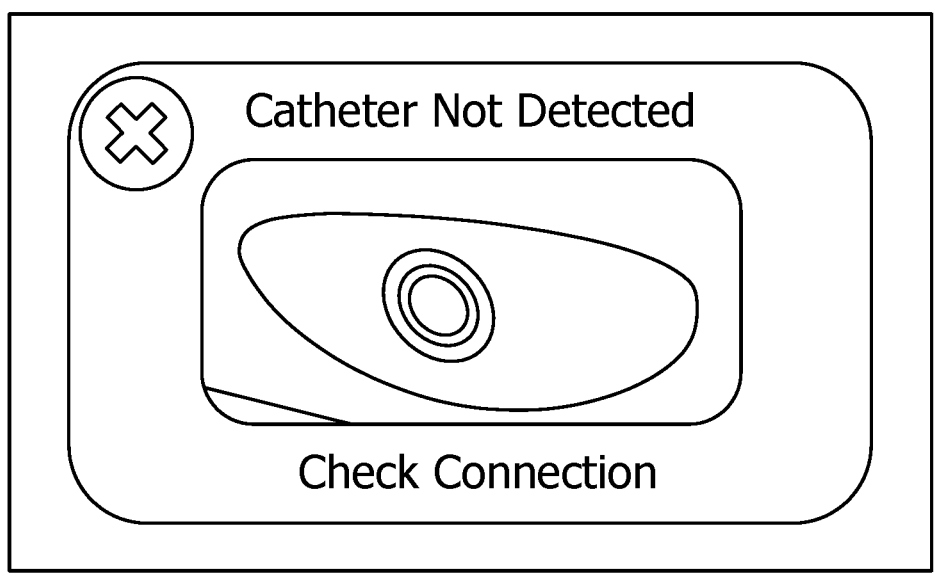
Figure 26:
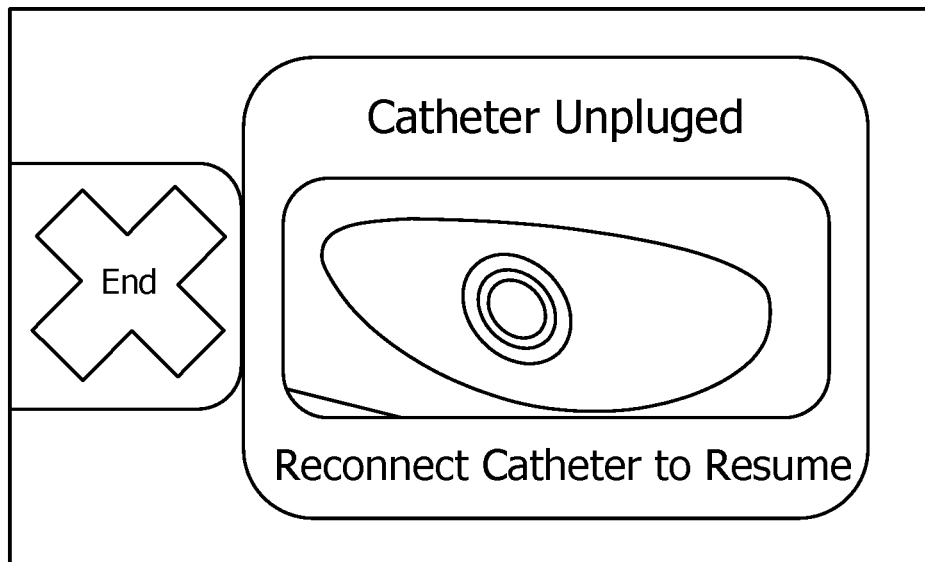

In some embodiments, upon completion of the "button hold" operation, the power controller 44 will then prompt the user to connect the catheter assembly 10. For example, as shown in FIG. 17, in some embodiments, the power controller will produce, via a user interface (e.g., the LCD display 50), a graphical depiction of the catheter connector 42 being coupled to the power controller 44. FIGS. 25 and 26 show graphical depictions indicating a connection status of the power controller. Although shown as being connected via a hard-wire connector, in other embodiments, the catheter assembly 10 can be coupled to the power controller 44 via a wireless connection.

After the catheter assembly 10 is coupled to the power controller 44, the lockout module and/or the control module can perform any number of validation tests to ensure that the catheter assembly 10 is properly functioning. Moreover, the control module can receive information from the electronic circuit system of the catheter assembly (e.g., factory calibration settings, calibration parameter(s), or the like) as described herein.

For example, after catheter connection is verified (e.g., a voltage is registered on the catheter connector 56), any of the modules of the power controller 44 can perform a test to determine if the ambient temperature from each temperature sensor (e.g., the temperature sensor(s) 123) is within an appropriate range. In some embodiments, the appropriate range can be between about 50F and about 120F. If the temperature on one channel is out of range, the power controller will refrain from using the defective channel for temperature control at any point in the procedure, and should display an error screen warning the user.

After catheter connection is verified (e.g., a voltage is registered on the catheter connector 56), the power controller 44 (and any of the software modules therein) can receive one or more calibration parameters from the electronic circuit system of the connected catheter assembly 10. The calibration parameters can be settings saved in the memory of the catheter assembly during manufacture, and can be unique to the particular catheter assembly in use. The calibration parameters can be any of the calibration parameters described herein, including an identification of a thermal profile associated with a particular class of patients, values associated with a fully open and fully closed position of the gap feedback sensor, or the like. As described herein, the power controller 44 can validate the operation of the catheter assembly 10 and/or select a predetermined algorithm based on the calibration parameters. In some embodiments, a control module of the power controller can receive (or read) calibration values from the EEPROM in the catheter assembly 10, and employ a checksum test to verify data integrity. If the catheter data fails the checksum, the power controller will display an error message to the user (see, e.g., the error message shown in FIG. 28).

Figure 29:
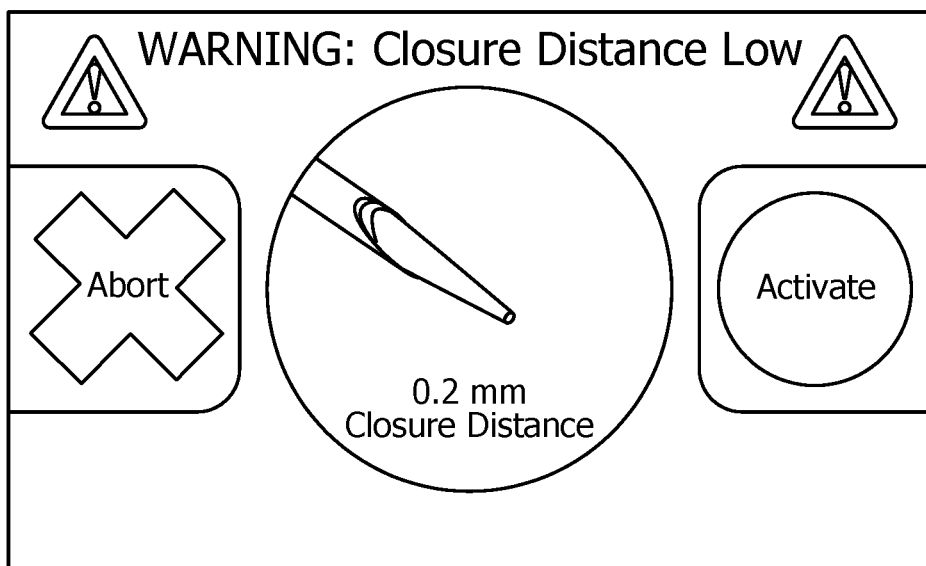
Figure 30:
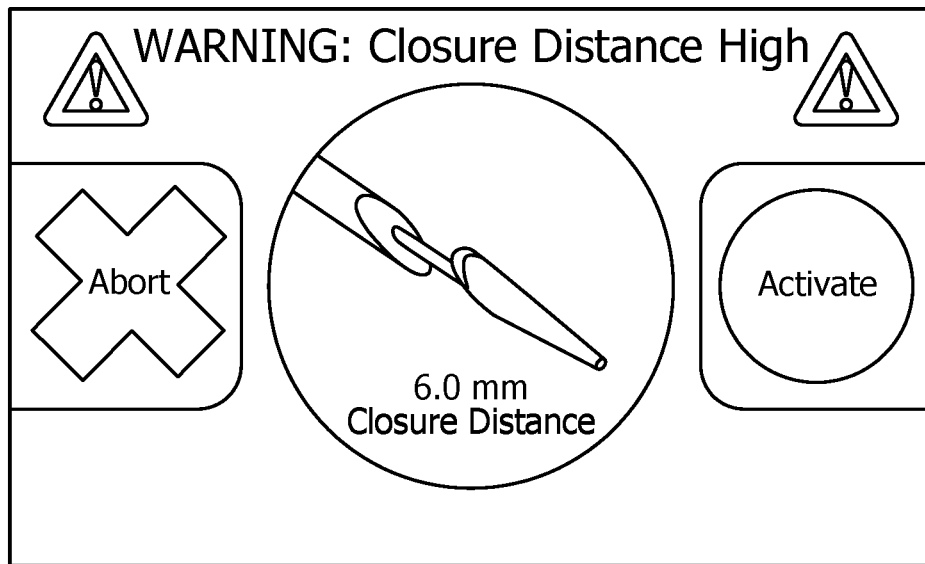
Figure 31:
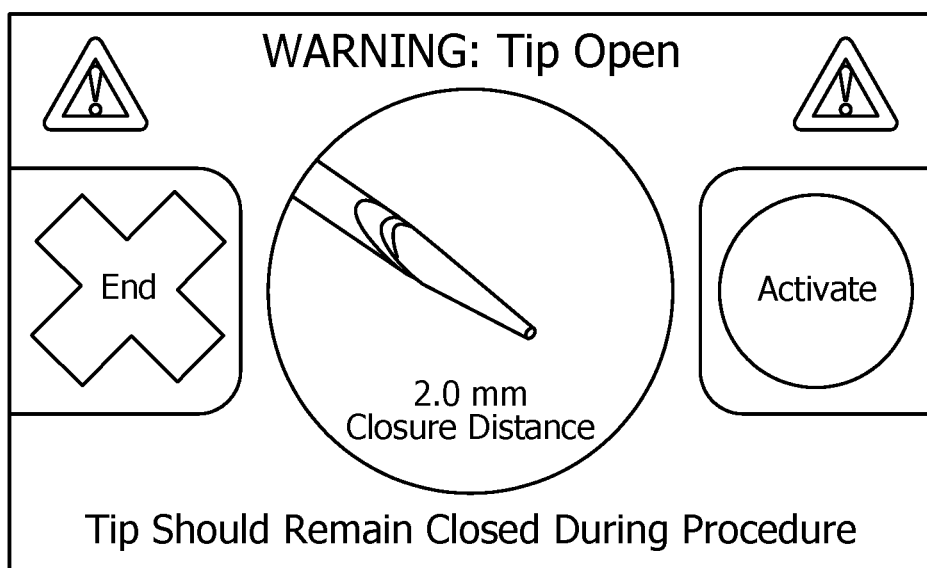
Figure 32:
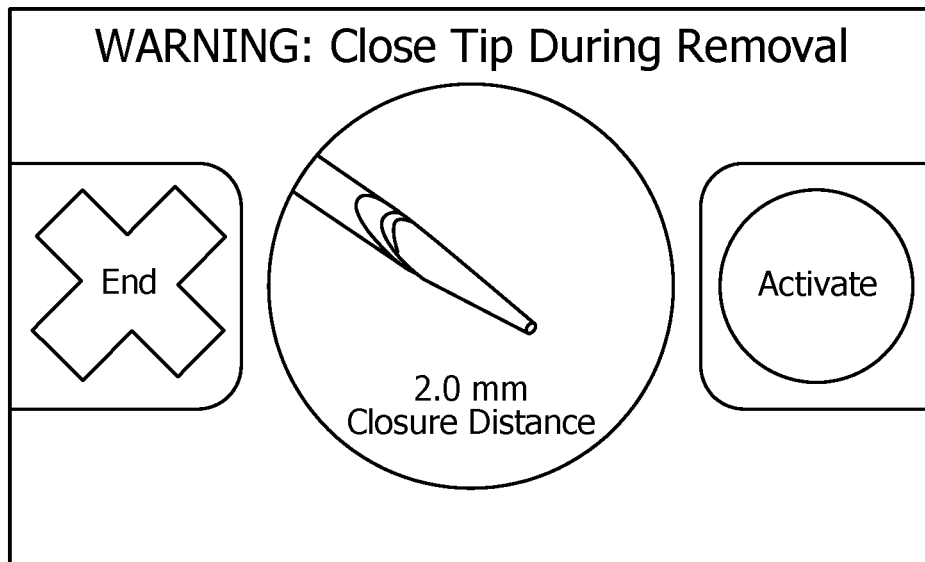
Figure 33:
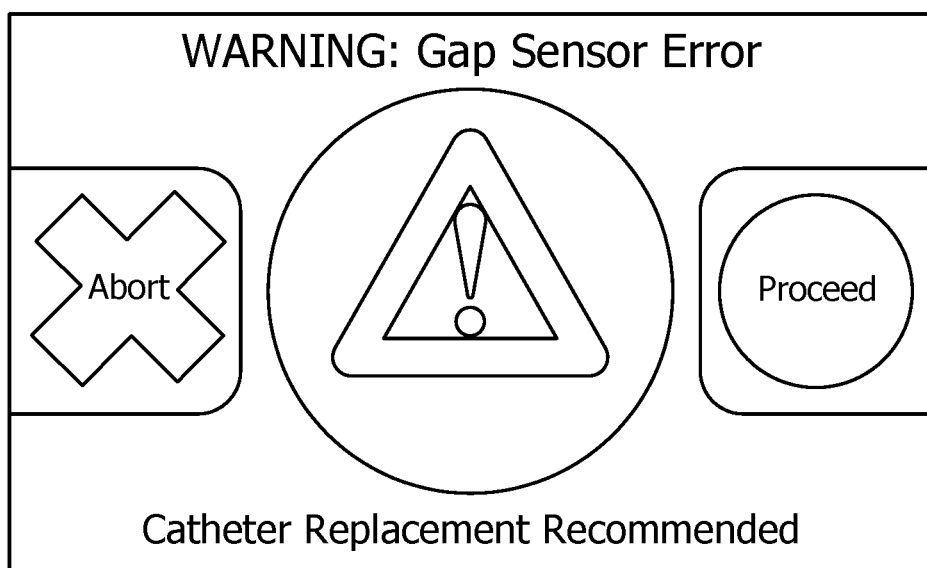

In some embodiments, the control module or the startup module can validate the gap feedback sensor based on the calibration parameters received. For example, in some embodiments, the calibration parameters include a first voltage (or first raw counts) associated with a fully closed setting (i.e., a gap of 0.0 mm) recorded during manufacture and a second voltage (or second raw counts) associated with a fully opened setting recorded during manufacture. The control module or startup module can compare a voltage received from the gap feedback sensor to validate the performance of the sensor. For example, if the voltage received from the gap feedback sensor is outside of the first voltage or the second voltage (i.e., the factor calibration settings), the power controller will produce a warning to the user stating that the gap feedback sensor is not properly functioning. FIGS. 29, 30, and 33 show images produced on the LCD display 50 indicating a fault condition with the gap feedback sensor.

In some embodiments, the lockout module will prevent further use of the catheter assembly (e.g., will prevent heating of the catheter assembly) when the gap feedback sensor is not functioning properly. In other embodiments, the power controller can prompt the user with the option to continue the procedure without the gap sensor feedback. In such embodiments, the control module will use a fixed value (e.g., 0.0 mm) to complete the procedure.

In some embodiments, the control module will receive a calibration parameter that is associated with one or more control settings that control the heating of the catheter assembly 10. Thus, the calibration parameter can be an identification associated with the control settings. Similarly stated, the calibration parameter can be a "Profile Identification" that identifies (or is used to select) the desired control settings. The control settings can be referred as a "thermal profile," and can any suitable parameters used to control the heating during fistula formation. Such parameters can include, for example, a first temperature set point, a second temperature set point, a duration (i.e., time) for each set point, a number of iterations of heating, and/or a duty cycle associated with the heat signals that are transmitted to the catheter assembly. An example thermal profile is provided in FIG. 10. As described herein, the power controller 44 will use the control settings to perform the desired "heat cycle" to create the fistula. In some embodiments, before allowing the user to initiate a heat cycle to produce the fistula, the power controller 44 will perform a catheter heating test (also referred to as a "warm up test") to ensure that the power controller and/or the catheter assembly can raise the temperature of the heating element 8 to a predetermined value within a predetermined time period. For example, in some embodiments, the warm up test can include heating the heating element 8 to a temperature of 125F (measured from either thermocouple) in under 2 seconds. If the catheter cannot pass this validation test, the control module will determine if there was voltage detected on the heater power supply. If voltage is detected, then the catheter assembly 10 is considered defective, and the power controller 44 will produce a warning to the user (see e.g., FIG. 28). If voltage was not detected, then the power controller 44 will display an error message indicating that the power controller (e.g., the power supply switch) is defective.

In some embodiments, before allowing the user to initiate a heat cycle to produce the fistula, the power controller 44 will verify that the gap distance is within the specified range for the selected heat cycle. If the gap distance is not in the appropriate range, the power control 44 can prompt the user to verify that the catheter assembly is in position before the procedure can be initiated (see, e.g., the warning screens in FIGS. 29-31).

In some embodiments, the power controller 44 can produce one or more graphical depictions of the catheter assembly 10 based on feedback from the gap feedback sensor, the temperature sensors, and internal control processes. The graphical depictions can show aspects of the catheter assembly during the heat cycle to assist the user in performing the fistula creation operation. Such graphical depictions can allow the user to graphically see the gap d between the proximal member 22 and the distal member 24 (see FIG. 4) as the gap changes during the procedure. Such can also allow the user to graphically see when heat is being applied to produce the fistula. By showing graphical depictions (or animations of the catheter assembly), the user can be presented with a clear image showing the procedure in process. Although described as being graphical in nature, the power controller 44 can also produce a series of different audible outputs to indicate certain aspects of the procedure (e.g. a different tone being emitted to signal heating of the catheter tip).

Figure 19:
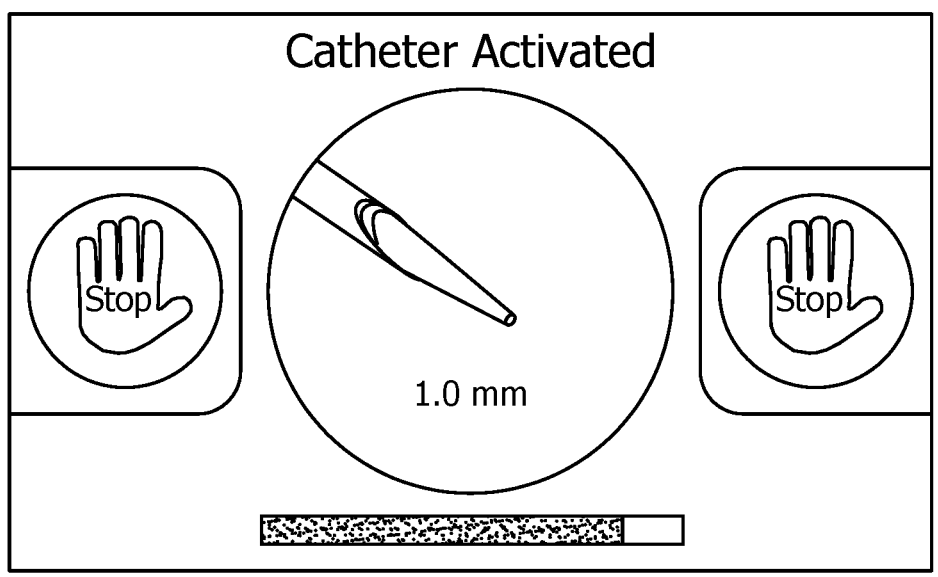

In some embodiments, the power controller 44 can display the status of the fistula creation procedure as a progress bar on the input/output device (e.g., the LCD display 50). An example of the status bar is shown in FIG. 19. In some embodiments, the graphical depiction can show at least one of the first tissue contact surface or the second tissue contact surface of the catheter assembly moving in response to a change in the distance d.

In some embodiments, the power controller 44 can display a heat indicator indicating that power is being supplied to the heating element 8. The heat indicator can include a series of colored regions surrounding the tip of the catheter assembly that is displayed to indicate that the tip is hot (see, e.g., the heat indicators shown in FIGS. 19 and 21).

In some embodiments, the power controller 44 can continuously update the images, status bars and/or text at a rate that allows the user to read the prompts without difficulty. For example, in some embodiments, the graphical animations showing the movement of the first contact surface or the second tissue contact surface can be in real time or quasi-real time so that the graphical animation is not choppy or irregular.

Thermal Profile Parameters and Logic Flow Chart

Exemplary parameters for each Heating Cycle of an identified exemplary Thermal Profile, or thermal control setting, are displayed in FIG. 10, a thermal profile array. Each cycle has a maximum number of iterations (pulses), and is controlled by the logic from the flow charts that follow. For each Set Temperature in each Thermal Cycle identified in the exemplary thermal profile, the hold time is the target time specified for each active heating pulse, and the Maximum Duration is an upper time tolerance limit for that pulse.

Figure 11:
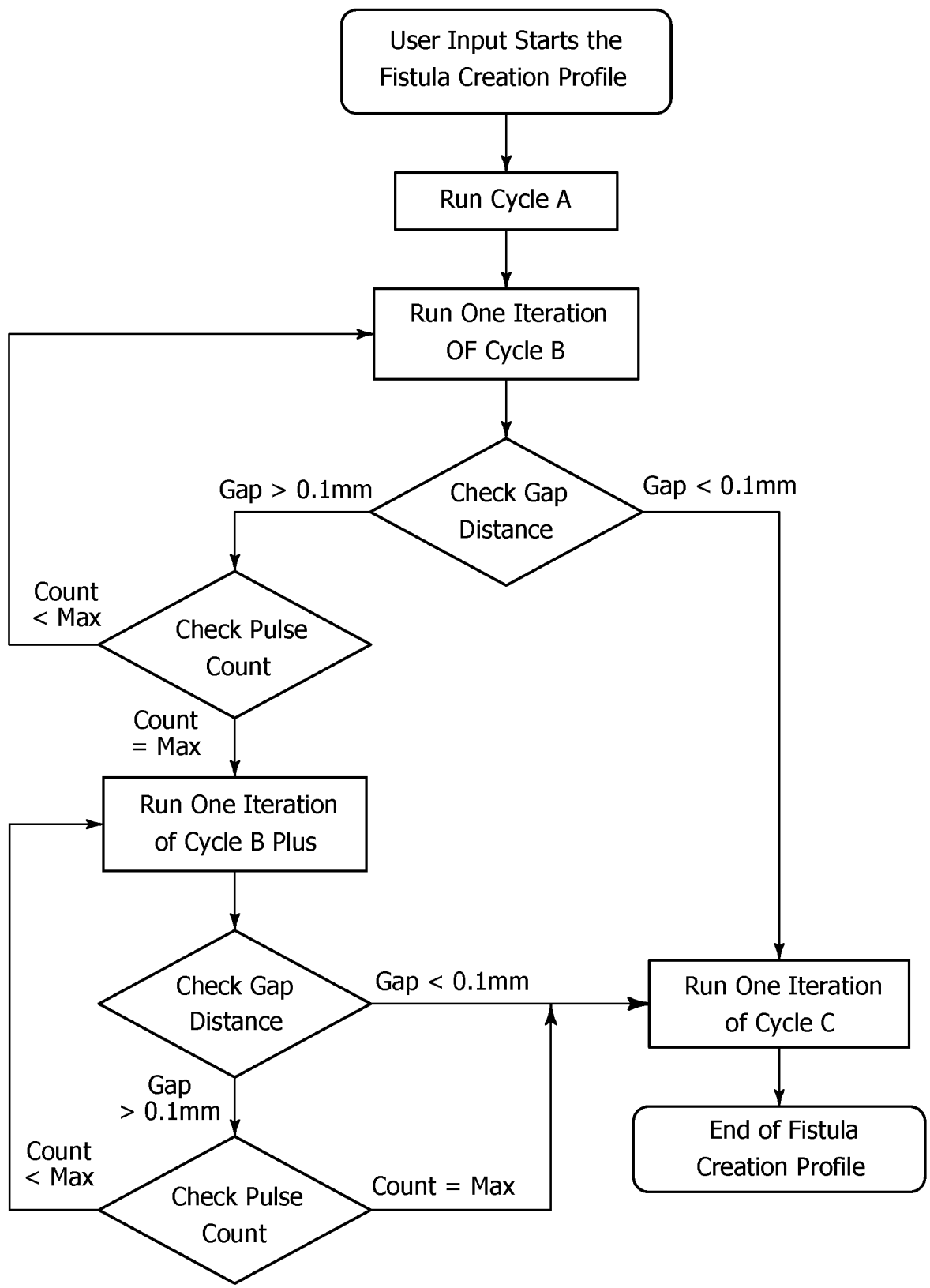
FIG. 11 is a flowchart provides the thermal profile progression logic which controls the transition between the heating cycles in the fistula creation profile for an exemplary system power controller constructed in accordance with the principles of the present invention.

The flowchart illustrated in FIG. 11 provides the Thermal Profile progression logic which controls the transition between the heating cycles in the Fistula Creation Profile. The User is prompted with instructions for progressing through the procedure, and is notified if any errors are encountered during the course of the procedure. It should be noted that, after the maximum six pulses specified in the thermal profile of FIG. 10 for thermal cycle C, the cycle times out, even if the gap distance remains greater than 0.1 mm, since the catheter is likely closed and has cut through and fused the vessel tissue walls, and excessive heating is to be avoided. The user can select an unlimited number of "Cycle Ds" to remove the device from the procedural site, in the event that the catheter has not fully closed after reaching its limit of six Cycle Cs.

Figure 12:
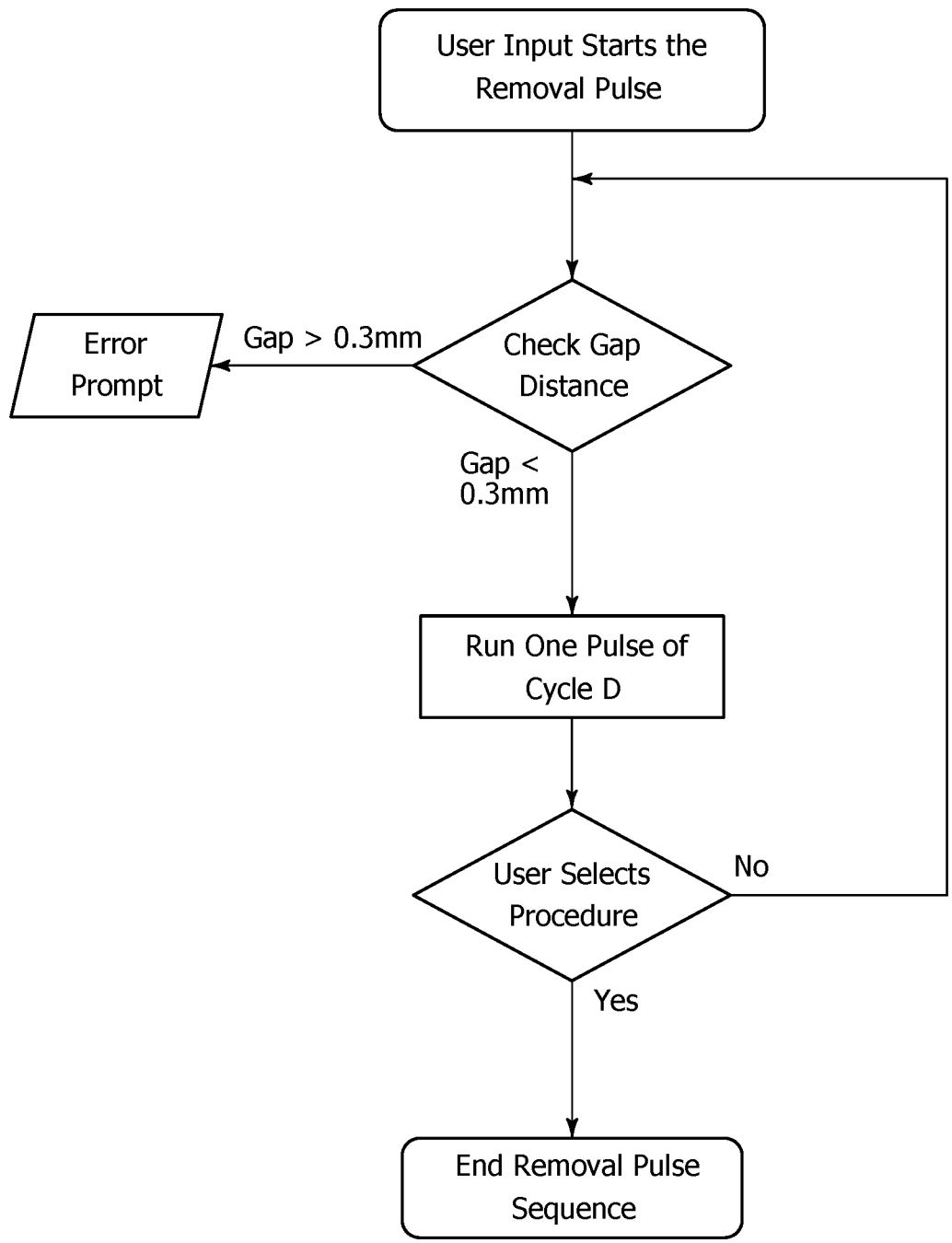
FIG. 12 is a flowchart illustrating the logic allowing the control of removal pulses as optionally provided by an exemplary system power controller constructed in accordance with the principles of the present invention.

Following the Fistula Creation Profile, the user has the option to conduct removal pulses. The logic which allows the control of removal pulses is contained in the flowchart set forth in FIG. 12.

Thus, in summary, the inventive systems and methods involve the use of a PID (Proportional-Integrative-Derivative) control loop to control temperatures, setpoints, pulse, and timing of the cutting and welding system during a control cycle. A position sensor or gap sensor in the catheter functions to limit and manage the cycles. A button on the handle or controller of the device functions to provide a manual removal pulse.

Figure 13:
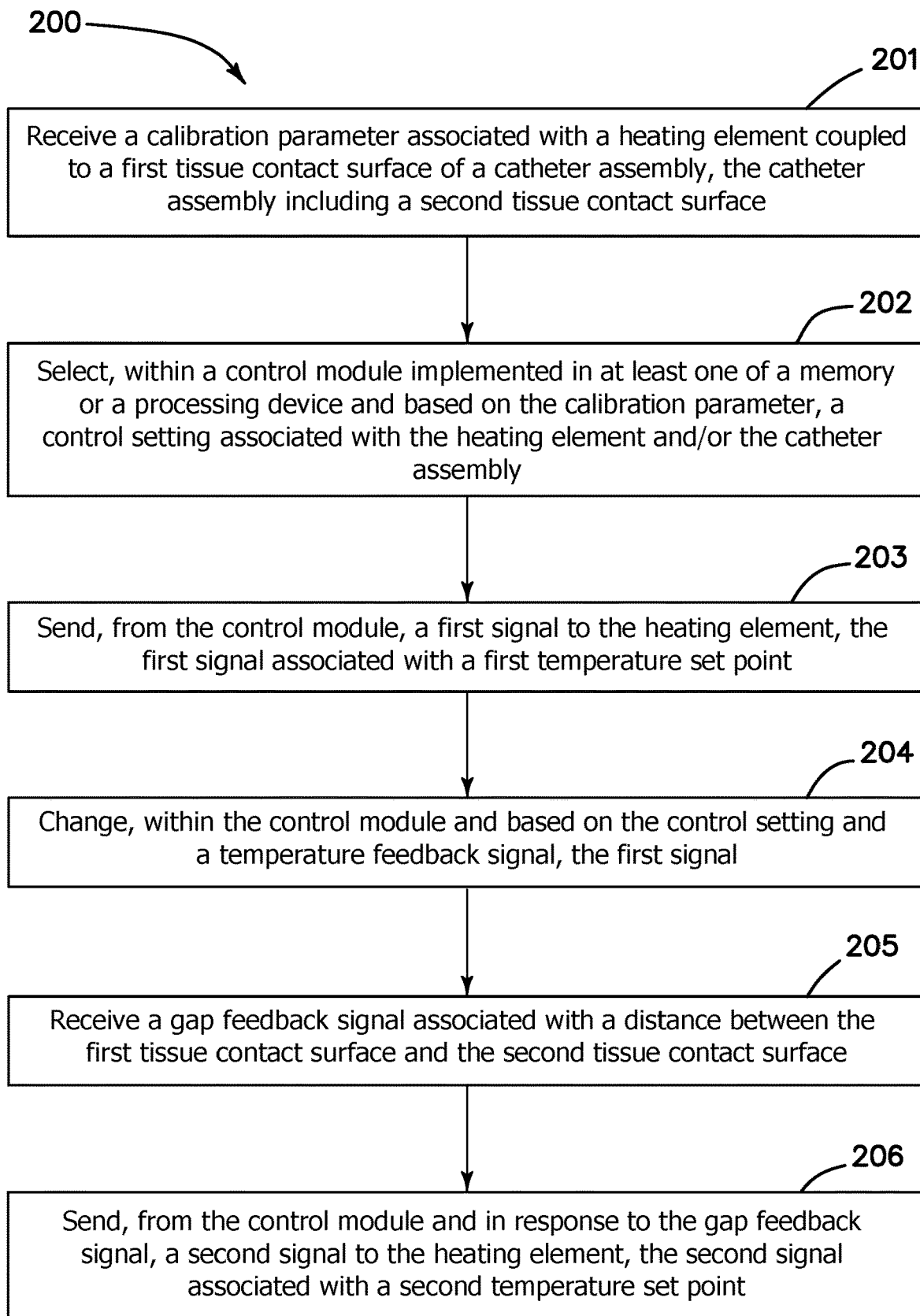
FIG. 13 is a flowchart illustrating a method of producing a fistula performed in accordance with the principles of the present invention.

FIG. 13 is a flow chart showing a method 200 of producing a fistula according to an embodiment. The method 200 can be performed using any of the power controllers and/or catheter assemblies described herein. The method includes receiving a calibration parameter associated with a heating element coupled to a first tissue contact surface of a catheter assembly, at 201. The catheter assembly can be, for example, the catheter assembly 10 described herein, and includes a second tissue contact surface. The calibration parameter can be any of the calibration parameters described herein, for example, an identification of a thermal profile, or the like. A control setting associated with the heating element and/or the catheter assembly is then selected based on the calibration parameter, at 202. The selecting can be performed within any suitable application or module of a power controller, including, for example, a control module implemented in at least one of a memory or a processing device.

The method 200 further includes sending, from the control module, a first signal to the heating element, at 203. The first signal, which can be a PWM signal, is associated with a first temperature set point. The first temperature set point can be, for example, an initial temperature set point of a thermal cycle. The first temperature set point can be, for example, any of the temperature set points shown in FIG. 10. The first signal is then changed based on the control setting and a temperature feedback signal, at 204. For example, in some embodiments, the first signal (or heat signal) can be changed to increase or decrease the power supplied to the heating element (e.g., the heating element 8) based on feedback from a temperature sensor (e.g., the temperature sensor(s) 123). The first signal can also be changed based on any of the control setting(s) such as a maximum duty cycle for the first signal, a duration during which the first temperature set point is to be maintained or the like. As described herein, the first signal can be changed within the control module, and can be changed based on a proportional/integral/derivative (PID) algorithm that regulates the Pulse Width Modulation (PWM) signal output to the heater power supply (and thus to the heating element).

The method further includes receiving a gap feedback signal associated with a distance between the first tissue contact surface and the second tissue contact surface, at 205. A second signal is then sent from the control module and in response to the gap feedback signal, at 206. The second signal, which is sent to the heating element (e.g., either directly or by way of the heater power supply), is associated with a second temperature set point. The second temperature set point can be, for example, a cool down temperature setting or a "removal pulse" that is initiated when the gap feedback signal indicates that the fistula has been successfully created.

Figure 14:
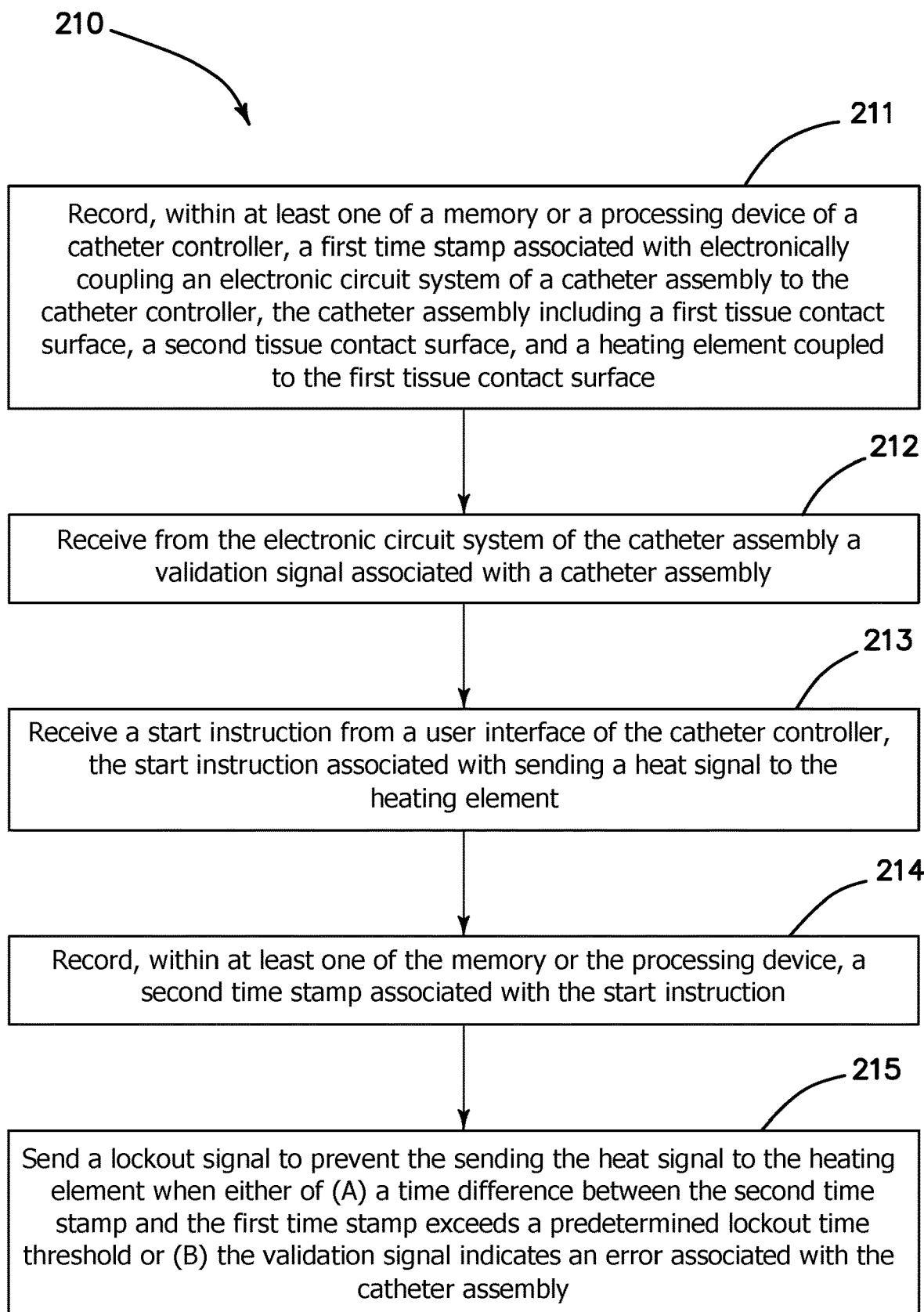
FIG. 14 is a flowchart illustrating a method of controlling a catheter assembly performed in accordance with the principles of the present invention.

FIG. 14 is a flow chart showing a method 210 of operating a catheter assembly in a manner that prevents reuse or operation of a defective catheter assembly, according to an embodiment. The method 210 can be performed using any of the power controllers and/or catheter assemblies described herein. The method includes recording, within at least one of a memory or a processing device of a catheter controller, a first time stamp associated with electronically coupling an electronic circuit system of a catheter assembly to the catheter controller, at 211. The catheter assembly can be, for example, the catheter assembly 10 described herein, and includes a first tissue contact surface, a second tissue contact surface, and a heating element coupled to the first tissue contact surface. A validation signal associated with a catheter assembly is then received from the electronic circuit system of the catheter assembly, at 212. The validation signal can be received from an EEPROM of the catheter assembly as described herein, and can be associated with at least one of a condition of a switch through which the heat signal is sent, a condition of a temperature sensor of the catheter assembly, or a heating test associated with the catheter assembly.

The method further includes receiving a start instruction from a user interface of the catheter controller, at 213. The start instruction is associated with sending a heat signal to the heating element. The start instruction can be, for example, an input from the user prompting the power controller to initiate a thermal cycle for creation of a fistula. A second time stamp associated with the start instruction is then recorded within at least one of the memory or the processing device, at 214. A lockout signal that prevents the sending the heat signal to the heating element is then sent when either of A) a time difference between the second time stamp and the first time stamp exceeds a predetermined lockout time threshold or B) the validation signal indicates an error associated with the catheter assembly, at 215.

Graphical User Interface (GUI)

In operation, in one exemplary method of operation, the power controller is turned on using the mains power switch 58 located on the power controller console 46. As the controller boots up, a button verification message is displayed on the screen 50, as shown in FIG. 11, referencing the multifunction buttons 52, 54, and instructing the user to test the buttons to verify their functionality. This action results in the display shown in FIG. 12, instructing the user to connect the catheter assembly 10 to the power controller system 44.

Figure 18:
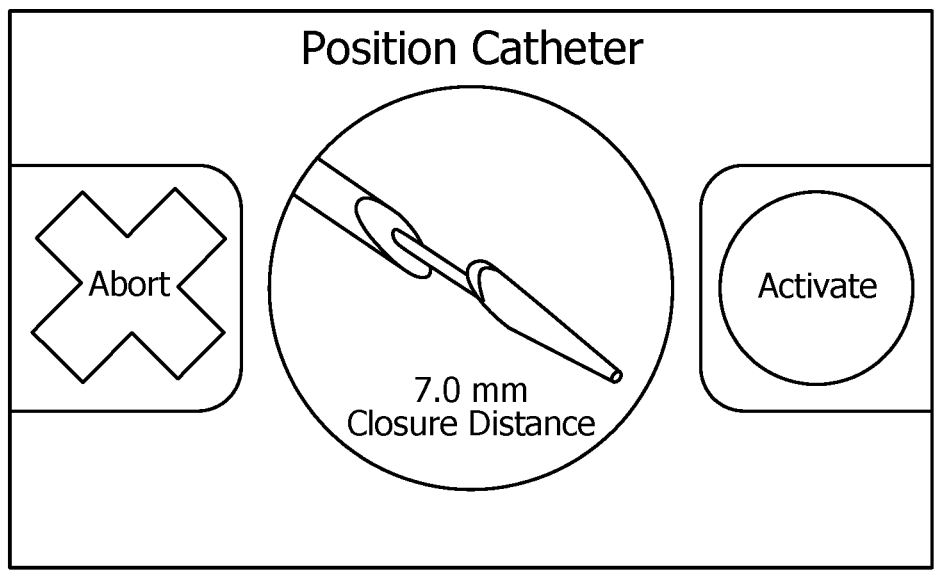

After the controller senses that the connection of the catheter assembly 10 to the power controller system 44 has been made, the user is instructed to position the catheter, via the display shown in FIG. 18. A position sensor (or gap sensor) detects the closure distance (gap distance d) between the distal surface 28 and the proximal surface 30 of the catheter, which is displayed for the user. Once the catheter is properly positioned at the procedural site, the "Activate" button (FIG. 18) is pressed by the user to initiate the application of thermal energy to the catheter for creation of the fistula. The power controller starts the thermal profile. The system displays the Catheter Activated screen (FIG. 19), which includes a progress bar and displays the closure distance.

Figure 20:
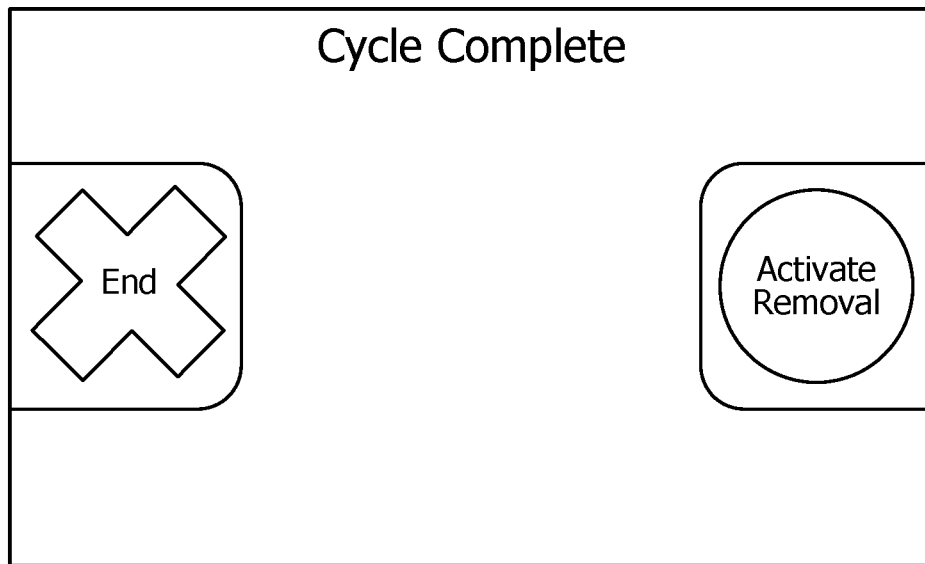
Figure 21:
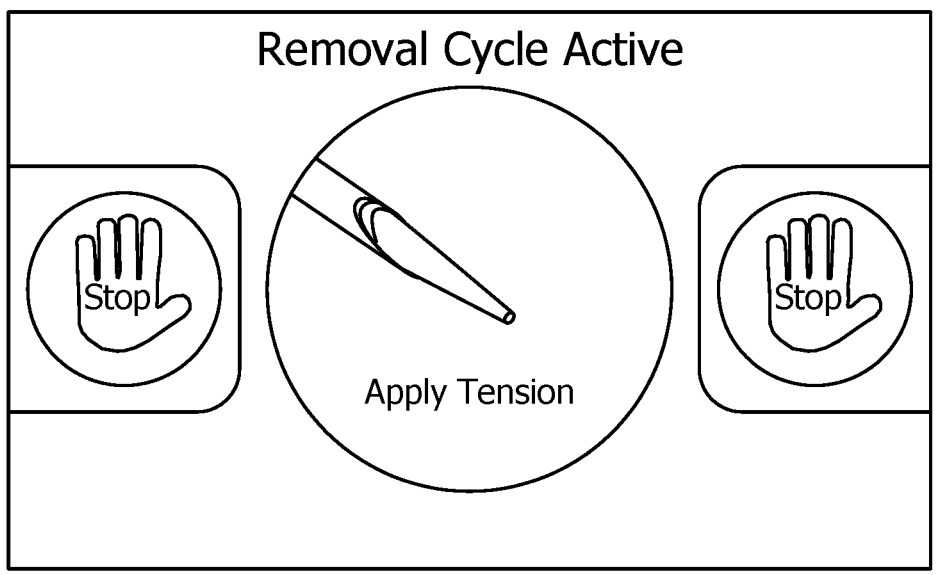
Figure 22:
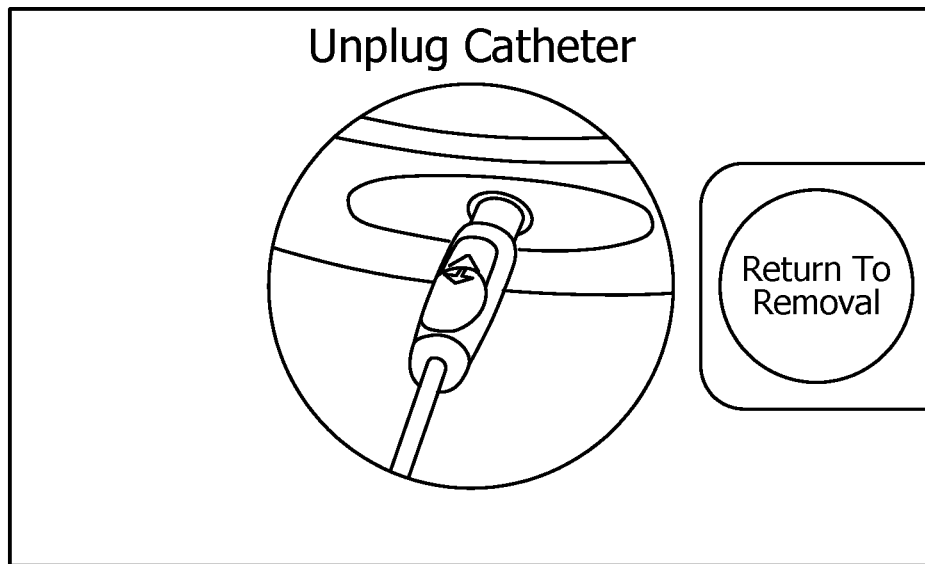
Figure 23:
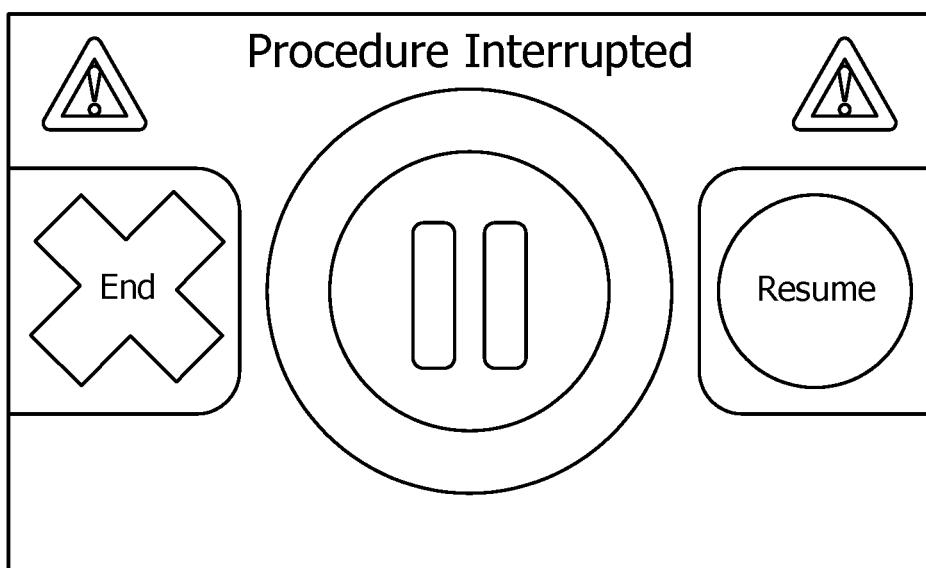

Once the gap distance has reached 0.0 mm, the power controller finishes the thermal cycle and displays the "Cycle Complete" screen shown in FIG. 20. At this juncture, slight tension is applied to the catheter. If the catheter does not release from the anastomosis, the user presses the "Activate Removal" button to start a removal pulse which applies energy to the catheter to aid in releasing the catheter. Multiple removal pulses may be employed to assist in the removal of the catheter. Activation of removal pulses generates the "Removal Cycle Active" screen shown in FIG. 21, after each cycle of which the "Cycle Complete" screen reappears. After the catheter has been removed, the "End" button is pressed (FIG. 20). The power controller then prompts the user to unplug the catheter (FIG. 22). When the catheter is unplugged, the screen of FIG. 17 reappears and remains in stand-by until a catheter is plugged in for a subsequent procedure. The power controller may be shut down by toggling the main power switch 58 to the off position.

FIGS. 23-32 illustrate various error and warning notification screens which may be generated if certain conditions present themselves. For example, if "Stop" is pressed during the program, the power controller will pause the thermal cycle and display the "Procedure Interrupted" message shown in FIG. 23. Pressing the "Resume" button will activate the catheter, while pressing the "End" button will end the program.

Figure 24:
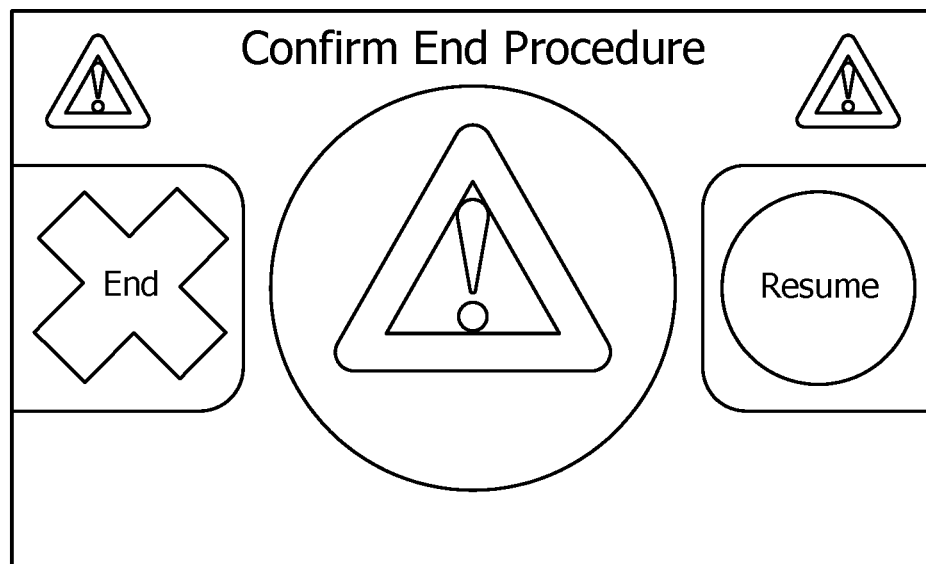

As shown in FIG. 24, if "Abort" or "End" is selected at any time, the power controller will ask for confirmation to end the procedure.

FIGS. 29-33 illustrate various screens which may be generated based on readings detected from the gap sensor, including warnings that the closure distance is too low (FIG. 29), the closure distance is too high (FIG. 30), the tip is open when it should be closed (FIG. 31), the tip is open during removal (FIG. 32), and there is a gap sensor error (FIG. 33).

Figure 15:
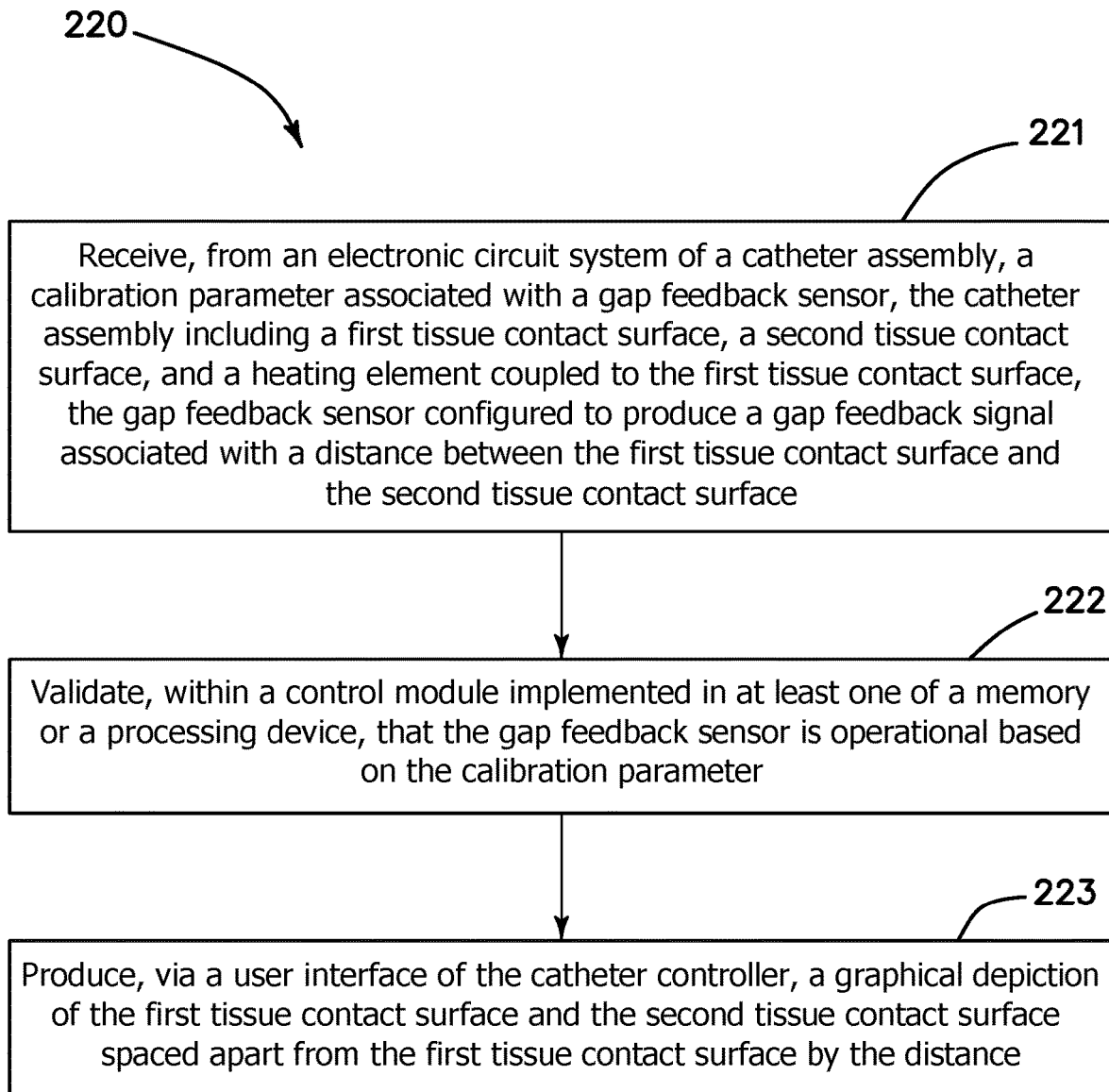
FIG. 15 is a flowchart illustrating a method of producing a display of the operation of a catheter assembly performed in accordance with the principles of the present invention.

FIG. 15 is a flow chart showing a method 220 of operating a catheter assembly in a manner that presents a graphical depiction showing the process of creating a fistula, according to an embodiment. The method 220 can be performed using any of the power controllers and/or catheter assemblies described herein. The method includes receiving, from an electronic circuit system of a catheter assembly, a calibration parameter associated with a gap feedback sensor, at 221. The catheter assembly can be, for example, the catheter assembly 10 described herein, and includes a first tissue contact surface, a second tissue contact surface, and a heating element coupled to the first tissue contact surface. The gap feedback sensor is configured to produce a gap feedback signal associated with a distance between the first tissue contact surface and the second tissue contact surface, as described herein. The method further includes validating, within a control module implemented in at least one of a memory or a processing device, that the gap feedback sensor is operational based on the calibration parameter, at 222. A graphical depiction of the first tissue contact surface and the second tissue contact surface spaced apart from the first tissue contact surface by the distance is then produced via a user interface of the catheter controller, at 223.

What is claimed is:

1. A method of operating a catheter assembly including a first tissue contact surface, a second tissue contact surface, a heating element coupled to the first tissue contact surface, and a gap feedback sensor configured to produce a gap feedback signal associated with a distance between the first tissue contact surface and the second tissue contact surface, the method comprising:
monitoring the gap feedback signal indicative of the distance between the first tissue contact surface and the second tissue contact surface;
producing via a user interface of the catheter assembly, a graphical depiction of the first tissue contact surface by the distance; and
producing, via the user interface of the catheter assembly, a gap distance warning when the gap feedback signal indicates that the distance is outside of a target gap range.

2. The method of claim 1, wherein the graphical depiction shows at least one of the first tissue contact surface or the second tissue contact surface moving in response to a change in the distance.

3. The method of claim 1, further comprising producing, via the user interface of the catheter assembly, a first gap distance warning including a graphical display indicating that the gap distance is too low when the gap feedback signal indicates that the distance is below the target gap range, and producing a second gap distance warning including a graphical display indicating that the gap distance is too high when the gap feedback signal indicates that the distance is above the target gap range.

4. The method of claim 3, wherein the first gap distance warning shows an image of the catheter assembly having a first gap between the contact surfaces, and the second gap distance warning shows an image of the catheter assembly having a second gap between the contact surfaces that is larger than the first gap.

5. The method of claim 4, wherein the first and second gap distance warnings show a numerical value of the distance between the contact surfaces.

6. The method of claim 1, further comprising:
receiving a start instruction from the user interface;
sending, from a control module of the catheter assembly, a heat signal to the heating element of the catheter assembly; and
producing, via the user interface, a heat indicator in response to the heat signal.

7. The method of claim 6, wherein the catheter assembly includes a temperature sensor coupled to the first tissue contact surface, the method further comprising:
receiving a temperature feedback signal from the temperature sensor, the heat indicator including a graphical indication associated with the temperature feedback signal.

8. The method of claim 6, wherein the heat indicator includes a graphical depiction and an audible tone, the graphical depiction indicating a hot portion of one of the first tissue contact surface or the second tissue contact surface.

9. The method of claim 6, wherein the heat indicator includes a series of colored regions surrounding a tip of the catheter assembly indicating that the tip is hot.

10. The method of claim 1, further comprising preventing initiation of a heating cycle to produce a fistula when the gap feedback signal indicates that the distance is outside of the target gap range.

* * * * *